US012146124B2

(12) United States Patent
Chakar et al.

(10) Patent No.: US 12,146,124 B2
(45) Date of Patent: Nov. 19, 2024

(54) BENEFIT-AGENT-CONTAINING DELIVERY PARTICLES HAVING HIGH CORE TO WALL RATIOS

(71) Applicant: Encapsys, LLC, Appleton, WI (US)

(72) Inventors: Fadi Selim Chakar, Neenah, WI (US); Linsheng Feng, Menasha, WI (US); Presley Genevie Neuman, Appleton, WI (US); Robert Stanley Bobnock, Menasha, WI (US); Johan Smets, Lubbeek (BE); An Pintens, Strombeek-bever (BE); Joana Andreia Lameiras Domingues, Brussels (BE)

(73) Assignee: Encapsys, LLC, Appleton, WI (US)

( * ) Notice: Subject to any disclaimer, the term of this patent is extended or adjusted under 35 U.S.C. 154(b) by 0 days.

(21) Appl. No.: 17/502,388

(22) Filed: Oct. 15, 2021

(65) Prior Publication Data

US 2023/0159863 A1 May 25, 2023

Related U.S. Application Data

(60) Provisional application No. 63/092,609, filed on Oct. 16, 2020.

(51) Int. Cl.
*C11D 3/50* (2006.01)
*B01J 13/16* (2006.01)
(Continued)

(52) U.S. Cl.
CPC .............. *C11D 3/505* (2013.01); *B01J 13/16* (2013.01); *C11D 3/0015* (2013.01); *C11D 3/3765* (2013.01); *C11D 3/3773* (2013.01)

(58) Field of Classification Search
CPC ..... C11D 3/505; C11D 3/0015; C11D 3/3765; B01J 13/16
See application file for complete search history.

(56) References Cited

U.S. PATENT DOCUMENTS 8,071,214 B2 12/2011 Schwantes
9,714,397 B2 7/2017 Feng et al.
(Continued)

FOREIGN PATENT DOCUMENTS

WO WO-2001062376 8/2001
WO WO-2005105291 11/2005
(Continued)

OTHER PUBLICATIONS

PCT International Search Report.
International Preliminary Report on Patentability.
Written Opinion of the International Searching Authority.

*Primary Examiner* — Liam J Heincer
*Assistant Examiner* — M. Reza Asdjodi
(74) *Attorney, Agent, or Firm* — Benjamin Mieliulis

(57) ABSTRACT

Populations of benefit agent delivery particles are disclosed, the particles having a core and a shell encapsulating the core, the shell comprising certain multifunctional (meth)acrylate-based polymers, along with processes for making and uses of such compositions. The delivery particle has a core to polymer wall ratio by weight from about 96:4 to about 99.5 to 0.5 and a volume-weighted particle size from about 30 to about 50 microns. The compositions deliver core content with a desired delivery profile, such as fragrance delivery at desired touchpoints with higher efficiency. The delivery particle has high pay load, yet exhibits decreased benefit agent leakage, and provides a desired delivery profile.

11 Claims, 2 Drawing Sheets

(51) Int. Cl.
*C11D 3/00* (2006.01)
*C11D 3/37* (2006.01)

(56) References Cited

U.S. PATENT DOCUMENTS

| | | | | |
|---|---|---|---|---|
| 2008/0118568 A1* | 5/2008 | Smets | ..................... | A61K 8/84 |
| | | | | 252/8.81 |
| 2011/0152147 A1* | 6/2011 | Smets | ................ | C11D 17/0039 |
| | | | | 510/516 |
| 2013/0164355 A1* | 6/2013 | Aussant | ............ | C11D 17/0013 |
| | | | | 510/516 |
| 2016/0058678 A1* | 3/2016 | Smets | ..................... | A61Q 5/02 |
| | | | | 510/513 |
| 2018/0064615 A1* | 3/2018 | Brahms | ............... | D06M 13/005 |
| 2018/0235893 A1* | 8/2018 | Zhang | ................... | A61Q 15/00 |
| 2018/0360706 A1* | 12/2018 | Dihora | ..................... | A61Q 5/02 |
| 2019/0184364 A1* | 6/2019 | Brahms | ..................... | C11B 9/00 |
| 2020/0222873 A1 | 7/2020 | Neuman et al. | | |
| 2022/0041961 A1* | 2/2022 | Smets | ..................... | B01J 13/185 |
| 2022/0153901 A1* | 5/2022 | Feng | ..................... | C11D 3/505 |
| 2022/0396750 A1* | 12/2022 | Smets | .................. | A61K 8/0241 |
| 2023/0056295 A1* | 2/2023 | Smets | .................. | C11D 3/0015 |
| 2023/0120922 A1* | 4/2023 | Smets | .................... | C11D 3/505 |
| | | | | 510/337 |
| 2023/0159863 A1* | 5/2023 | Chakar | ................ | C11D 3/3773 |
| | | | | 510/329 |

FOREIGN PATENT DOCUMENTS

| | | | | |
|---|---|---|---|---|
| WO | WO-2010079468 A2 * | 7/2010 | ............... | A61K 8/11 |
| WO | WO-2010084480 A2 * | 7/2010 | ............... | A61K 8/11 |
| WO | WO-2022081958 A1 * | 4/2022 | ............... | A61K 8/11 |
| WO | WO-2022082191 A1 * | 4/2022 | ......... | C11D 17/0039 |

* cited by examiner

BENEFIT-AGENT-CONTAINING DELIVERY PARTICLES HAVING HIGH CORE TO WALL RATIOS

FIELD OF INVENTION

The present application relates to benefit-agent-containing delivery particles, compositions comprising such particles, and processes for making and using such particles and compositions. The present invention relates to delivery particles having certain sizes, certain monomers (e.g., multifunctional (meth)acrylate monomers and certain core:wall polymer weight ratios.

BACKGROUND OF THE INVENTION

Benefit agents, such as perfumes, silicones, waxes, flavors, lubricants, agrichemical products, vitamins and fabric softening agents, are expensive and/or generally less effective or inefficient when employed at high levels in for example, personal care compositions, cleaning compositions, fabric care compositions, agrichemical products, adhesives, lubrication products, or coating applications. As a result, there is a desire to maximize the effectiveness of such benefit agents. One method of achieving such objective is to improve the delivery efficiencies of such benefit agents. In an effort to improve delivery efficiency, benefit agents have been encapsulated with a polymer wall using a variety of different compositions and constructs, but each tends to have drawbacks. For example, the particle size may be increased, but large particles tend to leak more than small particles and may not rupture at desired times. The relative amount of benefit agent in the core can be increased relative to the wall, but this, too, tends to result in relatively leaky particles as the walls become relatively thinner. Further, brittle capsules may prematurely rupture during the manufacturing process, for example due to mixing shear applied to a product composition. Additional wall material may reduce leakage and/or improve capsule strength, but then the particles may not adequately rupture at desired touchpoints, and payload or delivery efficiency is lower. Further, given the many known wall materials in the art, there is little guidance regarding what materials will work best for a given application or particle type.

There is a need for improved delivery particles that provide efficient benefit agent delivery, including relatively low leakage profiles and desirable release profiles.

The delivery particles are core-shell, and the particles having a polymer wall can comprise microcapsules, capsules and encapsulates, and such terms are synonyms for purposes of this application. Unfortunately, encapsulated benefit agents leak benefit agent over time, possibly via diffusion in the finished product. Even more compelling is a desire to increase core to polymer ratios to maximize usage efficiency. Leakage control however is even more challenging as the amount of polymer wall material is reduced. If the microcapsule leaks, the release of benefit agent at desired touchpoints is reduced. If such leakage is minimized, for example, by increasing the encapsulate shell strength, the benefit agent release at desired touchpoints may again be reduced because not enough benefit agent such as perfume is released from the capsules, or release is delayed beyond the optimal time for the intended application. This problem is particularly pronounced in certain end-use products for populations of delivery particles such as fabric treatment products, such liquid fabric enhancers, liquid laundry detergents, unit dose laundry detergents and granule/powdered laundry detergents that comprise such encapsulates. An encapsulate having a high core content, yet able to release at desired touchpoints, would be commercially advantageous for increased efficiency in benefit agent delivery, such as fragrance delivery.

SUMMARY OF THE INVENTION

The present disclosure relates to delivery particles having certain sizes, monomers, and core:wall ratios. Applicants disclose a composition and processes of making, of a population of delivery particles, which can be usefully dispersed in the form of a liquid or emulsion, or as an aqueous slurry or dried or dewatered to a powder form or granular composition, that has an unexpectedly high pay load, high core to wall ratio, yet which exhibits decreased benefit agent leakage, and/or which provides more efficient benefit agent delivery, or a more desired and beneficial release profile. The present invention relates to benefit agent containing delivery particles comprising a core material and a wall material that encapsulates the core material. The present invention also relates to compositions comprising said particles, and processes for making and using such particles and compositions, and articles of manufacture comprising such particles.

The invention provides encapsulates that have a desired core to polymer wall loading and desirable benefit agent release characteristics based on selection of monomer, oligomer or prepolymer combinations that can provide a desired core loading level while retaining the core with low leakage while optimally delivering and releasing the core, such as fragrance or other benefit agent, to a situs. However, in the art, there is little to no guidance as to how to overcome the challenges to achieve high core content, retain the core content with low leakage, and deliver that core content at desired touch points whether in laundry, fabric care or other situs. Surprisingly, Applicants recognized that a high performing encapsulate can be constructed from a unique emulsion derived at least in part from one or more oil-soluble or dispersible multifunctional (meth)acrylate monomers or oligomers having at least three, or even at least four, radical polymerizable functional groups wherein at least one of the radical polymerizable groups is acrylate or methacrylate wherein the delivery particle has a core to polymer wall ratio by weight from about 96:4 to about 99.5: to 0.5, or even from about 98:2 to about 99:1; and said delivery particle having a volume-weighted particle size from about 30 to about 50 microns. This combination surprisingly is able to deliver core content with a desired odor profile, such as at desired touchpoints with higher efficiency than prior art combinations.

In one aspect, the invention teaches a population of delivery particles, the delivery particles comprising a core and a polymer wall encapsulating said core, wherein:

the core comprises an oily medium comprising a benefit agent and a partitioning modifier wherein the partitioning modifier comprises from 5% to 55% by weight of the core;

the polymer wall comprises a (meth)acrylate polymer derived, at least in part, from (a) one or more oil-soluble or dispersible multifunctional (meth)acrylate monomers or oligomers and optionally at least one initiator, the one or more oil-soluble or dispersible multifunctional (meth)acrylate monomers or oligomers having at least three, and preferably at least four, at least five, or even at least six radical polymerizable functional groups wherein the radical polymerizable functional groups are each independently selected from acrylate, methacrylate, styrene, allyl, vinyl, glycidyl, ether, epoxy, carboxyl, or hydroxyl, with the proviso that at least one of the radical polymerizable groups is acrylate or methacrylate; and (b) optionally at least one water soluble or dispersible initiator, and optionally at least one mono- or multifunctional (meth)acrylate monomer and/or oligomer;

said delivery particles having a core to polymer wall ratio by weight from about 96:4 to about 99.5:0.5, or even about 98:2 to about 99:1; and said delivery particles having a volume-weighted particle size from about 30 to about 50 microns.

The delivery particles comprise the core and polymer wall present in a weight ratio of from about 97:3 to about 99:1, more preferably from about 98:2 to about 99:1. In the population of delivery particles the one or more oil-soluble or dispersible multifunctional (meth)acrylate monomers or oligomers comprise at least four, preferably at least five, preferably six, radical polymerizable functional groups. The radical polymerizable functional groups can be each independently selected from the group consisting of acrylate and methacrylate. The oil soluble or dispersible multifunctional (meth)acrylate monomer or oligomer can comprise a multifunctional aromatic urethane acrylate such as a tri-, tetra-, penta-, or hexafunctional aromatic urethane acrylate. In another aspect the oil soluble or dispersible multifunctional monomers or oligomers can comprise a multifunctional aliphatic urethane acrylate or can further comprise a monomer selected from an amine methacrylate, an acidic methacrylate, or a combination thereof.

In a further aspect, the (meth)acrylate polymer of the polymer wall of the population of delivery particles is a reaction product derived from the oil-soluble or oil-dispersible multifunctional (meth)acrylate, but also a second monomer, and/or a third monomer, wherein the second monomer comprises a basic (meth)acrylate monomer, and wherein the third monomer comprises an acidic (meth)acrylate monomer. In another aspect the (meth)acrylate polymer of the polymer wall can be further derived from a water-soluble or water-dispersible mono- or multifunctional (meth)acrylate monomer or oligomer, preferably selected from the group consisting of amine (meth) acrylates, acidic (meth)acrylates, polyethylene glycol di(meth)acrylates, ethoxylated monofunctional (meth)acrylates, ethoxylated multi-functional (meth)acrylates, other (meth)acrylate monomers, other (meth)acrylate oligomers, and mixtures thereof. If an emulsifier or surfactant is used to aid in emulsification, the polymer wall of the delivery particles can further comprise a surfactant or polymeric emulsifier entrapped in the polymer wall. Preferably the polymeric emulsifier comprises polyvinyl alcohol. Preferable, the (meth)acrylate polymer of the polymer wall is further derived, at least in part, from at least one water-soluble or water-dispersible, and/or oil-soluble or oil-dispersible free radical initiator.

In the population of delivery particles according to the invention, when the benefit agent is selected to be a fragrance, preferably the fragrance comprises perfume raw materials characterized by a log P of from about 2.5 to about 4.

In embodiments, the partitioning modifier of the population of delivery particles described herein can selected from the group consisting of isopropyl myristate, vegetable oil, modified vegetable oil, mono-, di-, and tri-esters of C4-C24 fatty acids, propan-2-yl tetradecanoate, dodecanophenone, lauryl laurate, methyl behenate, methyl laurate, methyl palmitate, methyl stearate, and mixtures thereof. The population is characterized by an average volume weighted median fracture strength of from about 0.2 to about 10 MPa, preferably from about 0.5 to about 8 MPa, more preferably from about 0.5 to about 5 MPa. In embodiments, for a constant core to polymer wall ratio, the leakage of the population delivery particles can decrease as size of the delivery particle increases, within the range of from 30 to 50 um.

The polymer wall of the population of benefit agent delivery particles can further comprise a coating material, wherein the coating material is selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines, copolymers of polyvinyl amines, and mixtures thereof.

In an aspect, the invention discloses a novel process of making a population of delivery particles comprising a core and a polymer wall encapsulating said core, the process comprising the steps of: i) dissolving or dispersing into one or more oil phases core materials comprising a benefit agent and a partition modifier, and dissolving or dispersing into the one or more oil phases one or more oil-soluble or dispersible multifunctional (meth)acrylate monomers having at least three, and preferably at least four, radical polymerizable functional groups wherein the radical polymerizable functional groups are each independently selected from acrylate, methacrylate, styrene, allyl, vinyl, glycidyl ether, epoxy, carboxyl, or hydroxyl, with the proviso that at least one of the radical polymerizable groups is acrylate or methacrylate; ii) providing a water phase comprising an emulsifier or surfactant; iii) emulsifying the oil phase into the water phase under high shear agitation to form an oil-in-water emulsion comprising droplets of the core materials and oil phase dispersed in the water phase, the droplets comprising the population of delivery particles' core; iv) reacting the dissolved or dispersed monomers by heating or actinic irradiation of the emulsion thereby forming a polymer wall at an interface of the droplets and the water phase. Of the particles formed by the process, the partitioning modifier comprises from 5% to 55% by weight of the delivery particles' core; said delivery particles have a core to polymer wall ratio by weight from 96:4 to about 99.5:0.5, and said delivery particles having a volume weighted median particle size from 30 to 50 microns.

Surprisingly, in certain embodiments, the reacting step can even be carried out in the substantial absence of initiator. In further embodiments, a further step of addition to the one or more water phases and/or to the one or more oil phases, or to both phases, is included to add one or more free radical initiators, thereby providing a source of free radicals upon activation by heat, or even by actinic radiation. The further addition step can comprise dissolving or dispersing into the water phase or oil phase, or both, a free radical initiator at an amount greater than 0% to 5% by weight of the respective phase.

In an aspect, the process of the invention comprises a further step of dissolving or dispersing into the water phase one or more mono- or multi-functional (meth)acrylate monomers and/or oligomers. In certain embodiments, a multifunctional (meth)acrylate monomers having radical polymerizable functional groups is used, and the multifunctional (meth)acrylate monomer can even be a multifunctional aromatic urethane acrylate, such as a tri-, tetra-, penta-, or hexafunctional aromatic urethane acrylate.

Alternatively, the dissolving or dispersing step into the oil phase can comprise in addition dissolving or dispersing into the oil phase or phases one or more multifunctional aliphatic urethane acrylates; or can comprise the additional step of dissolving or dispersing into the oil phase oil one or more of an amine methacrylate or an acidic methacrylate. In an yet further embodiment, the process of the invention can include a further step comprising dissolving or dispersing in into either the water or oil phases, or both, of one or more amine methacrylates, acidic methacrylates, polyethylene glycol di(meth)acrylates, ethoxylated mono- or multi-functional (meth)acrylates, or (meth)acrylate monomers and/or oligomers. In another aspect, the partitioning modifier dissolved or dispersed into the one or more oil phases can be selected from the group consisting of isopropyl myristate, vegetable oil, modified vegetable oil, mono-, di-, and tri-esters of C4-C24 fatty acids, propan-2-yl tetradecanoate, dodecanophenone, lauryl laurate, methyl behenate, methyl laurate, methyl palmitate, methyl stearate, and mixtures thereof.

In certain embodiments, for a constant core to polymer wall ratio, the leakage of the delivery particle population decreases as size of the delivery particle increases, within the range of from 30 to 50 um.

DETAILED DESCRIPTION OF THE INVENTION

Figure 1:
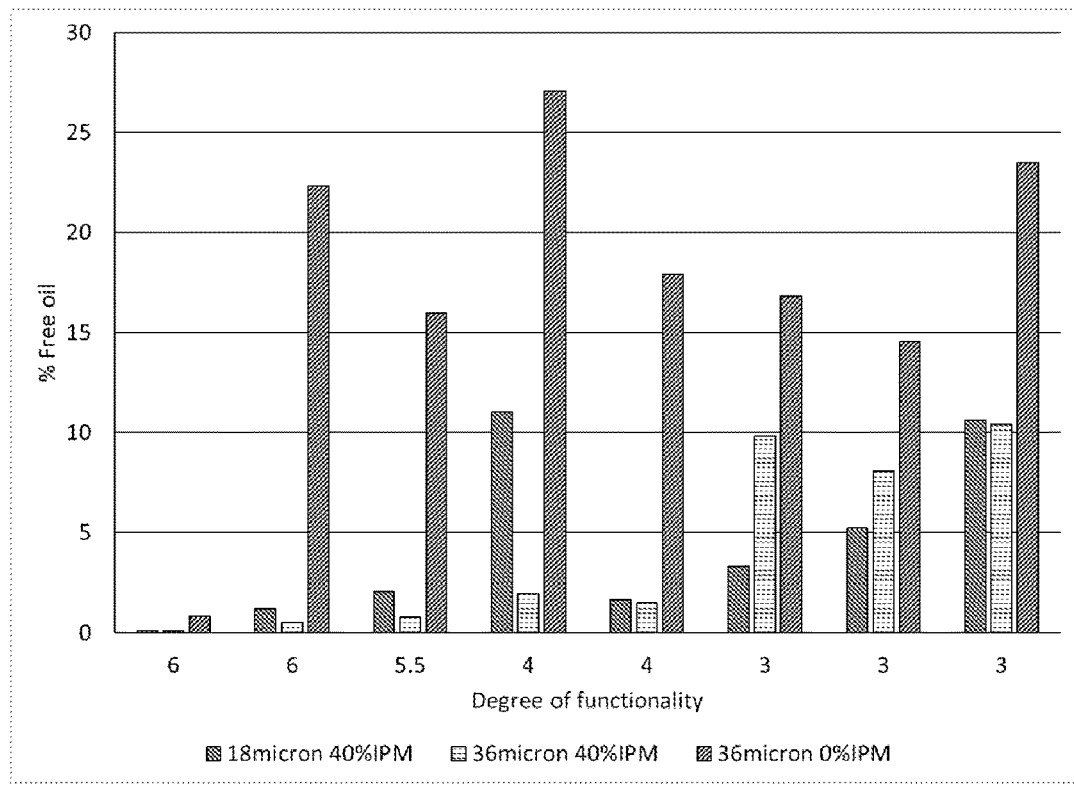
FIG. 1 is a graph depicting percent free oil of slurries prepared according to the invention, prepared at 18 and 36 micron diameter, and compared to 36 micron microcapsules in the absence of isopropyl myristate using (meth)acrylate monomers of various functionality as indicated.

The present disclosure relates to populations of delivery particles. The delivery particles (or simply "particles", as used herein) are core/shell particles that include a benefit agent, and typically a partitioning modifier, comprising the core which is surrounded by a polymer wall.

It has surprisingly been found that delivery particles having desirable leakage profiles and release profiles can be formed by careful selection of a combination of factors—for example, core-to-wall-polymer weight ratios, particle size, and monomers used to form the polymer wall. As a result of the combinations described herein, it is possible to formulate delivery particles that have unexpectedly high pay loads, yet which still exhibit decreased benefit agent leakage, and provide a desired benefit agent release profile, such as odor-release profile.

The present disclosure relates to encapsulates that include particular polymers in the walls of the encapsulates. Without wishing to be bound by theory, it is believed that making the described choices in encapsulate design results in encapsulates that provide improved performance profiles.

In prior art systems, leakage tends to increase with increasing particle size. A surprising aspect of presently described particles is the unique combination of monomers, oligomers and/or prepolymers yielding a core shell microcapsule as a benefit agent particle wherein as the median particle size of the benefit agent particle increases, the one-week leakage decreases in a relative comparison to systems without the inventive combination.

In the art leakage generally increases as benefit agent particles, such as core shell encapsulates and microcapsules, increase in size. The present disclosure discloses larger size core shell benefit agent delivery particles that surprisingly achieve lower leakage relative to comparable sized particles of the art.

The present disclosure relates to high payload particles, such as 96 to 98% or even to 99.5% core on the basis of the ratio by weight of the core to the shell.

The composition of particles of the present disclosure are relatively large particles, yet of lower leakage and of higher strength as compared to particles of the art.

The encapsulates and related methods of the present disclosure are described in more detail below.

Definitions

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein, "consumer product," means baby care, beauty care, fabric & home care, family care, feminine care, and/or health care products or devices intended to be used or consumed in the form in which it is sold, and not intended for subsequent commercial manufacture or modification. Such products include but are not limited to diapers, bibs, wipes; products for and/or methods relating to treating human hair, including bleaching, coloring, dyeing, conditioning, shampooing, styling; deodorants and antiperspirants; personal cleansing; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; adult incontinence products; products and/or methods relating to oral care including toothpastes, tooth gels, tooth rinses, denture adhesives, tooth whitening; over-the-counter health care including cough and cold remedies; pest control products; and water purification.

As used herein, "other than a consumer product" means feedstocks used neat or used for manufacture of industrial products. Such feedstocks include dry capsules, microcapsules, slurries of microcapsules, microcapsule aggregates, microcapsule powders, microcapsule dispersions, microcapsule coating and binding materials with microcapsules. End use applications can include, but are not limited to, coatings for substrates, raw material slurries, slurries of benefit agent delivery parties for benefit agents such as industrial lubricants such as for injection wells, cakes or powders of benefit agent delivery particles as raw materials in the manufacture of consumer or other products, slurries for delivery of beneficial agents such as slurries for industrial uses such as delivery of fragrances, lubricants or other actives.

As used herein, the phrase "benefit agent containing delivery particle" encompasses microcapsules having a core comprising a benefit agent, for example perfume including but not limited to microcapsules encapsulating perfumes, lubricants, oils, waxes, hydrocarbons, essential oils, lipids, skin coolants, sunscreens, antioxidants, malodor reducing agents, odor-controlling materials, fragrances, insect and moth repelling or controlling agents, agricultural actives, colorants, bodying agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, optical brighteners, color restoration/rejuvenation agents, anti-fading agents, whiteness enhancers, anti-abrasion agents, wear resistance agents, UV protection agents, sun fade inhibitors, enzymes, water proofing agents, shrinkage resistance agents, antibacterial actives, antiperspirant actives, dyes, and mixtures thereof.

As used herein, the terms "particle", "delivery particle" "benefit agent containing delivery particle", "encapsulate", "capsule" and "microcapsule" are synonymous, unless indicated otherwise.

As used herein, reference to the term "(meth)acrylate" or "(meth)acrylic" is to be understood as referring to both the acrylate and the methacrylate versions of the specified monomer, oligomer and/or prepolymer. For example, "allyl (meth)acrylate" indicates that both allyl methacrylate and allyl acrylate are possible, similarly reference to alkyl esters of (meth)acrylic acid indicates that both alkyl esters of acrylic acid and alkyl esters of methacrylic acid are possible, similarly poly(meth)acrylate indicates that both polyacrylate and polymethacrylate are possible. Poly(meth)acrylate materials are intended to encompass a broad spectrum of polymeric materials including, for example, polyester poly (meth)acrylates, urethane and polyurethane poly(meth)acrylates (especially those prepared by the reaction of an hydroxyalkyl (meth)acrylate with a polyisocyanate or a urethane polyisocyanate), methylcyanoacrylate, ethylcyanoacrylate, diethyleneglycol di(meth)acrylate, trimethylolpropane tri(meth)acrylate, ethylene glycol di(meth)acrylate, allyl (meth)acrylate, glycidyl (meth)acrylate, (meth)acrylate functional silicones, di-, tri- and tetraethylene glycol di(meth)acrylate, dipropylene glycol di(meth)acrylate, polyethylene glycol di(meth)acrylate, di(pentamethylene glycol) di(meth)acrylate, ethylene di(meth)acrylate, neopentyl glycol di(meth)acrylate, trimethylol propane tri(meth)acrylate, ethoxylated bisphenol A di(meth)acrylates, bisphenol A di(meth)acrylates, diglycerol di(meth)acrylate, tetraethylene glycol dichloroacrylate, 1,3-butanediol di(meth)acrylate, neopentyl di(meth)acrylate, trimethylolpropane tri(meth) acrylate, and various multifunctional(meth)acrylates. Monofunctional (meth)acrylates, i.e., those containing only one (meth)acrylate group, may also be advantageously used. Typical mono(meth)acrylates include 2-ethylhexyl (meth) acrylate, 2-hydroxyethyl (meth)acrylate, cyanoethyl (meth) acrylate, 2-hydroxypropyl (meth)acrylate, p-dimethylaminoethyl (meth)acrylate, lauryl (meth)acrylate, cyclohexyl (meth)acrylate, tetrahydrofurfuryl (meth)acrylate, chlorobenzyl (meth)acrylate, aminoalkyl(meth)acrylate, various alkyl(meth)acrylates and glycidyl (meth)acrylate. Mixtures of (meth)acrylates or their derivatives as well as combinations of one or more (meth)acrylate monomers, oligomers and/or prepolymers or their derivatives with other copolymerizable monomers, including acrylonitriles and methacrylonitriles may be used as well.

For ease of reference in this specification and in the claims, the term "monomer" or "monomers" as used herein with regard to the polymer wall is to be understood as monomers but also is inclusive of oligomers or monomers, and prepolymers formed of the specific monomers.

All temperatures herein are in degrees Celsius (° C.) unless otherwise indicated. Unless otherwise specified, all measurements herein are conducted at 20° C. and under atmospheric pressure.

In all embodiments of the present disclosure, all percentages are by weight of the total composition, unless specifically stated otherwise. All ratios are weight ratios, unless specifically stated otherwise.

The test methods disclosed in the Test Methods section of the present application should be used to determine the respective values of the parameters of the invention.

Unless otherwise noted, all component or composition levels are in reference to the component or composition exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Populations of Benefit Agent Delivery Particles

The compositions and products of the present disclosure comprise benefit agent delivery particles. The particles typically comprise a core and a shell, where the shell encapsulates the core, the shell being a polymer wall.

For clarity, a multiplicity of particles may be referred to herein as a population of the benefit agent delivery particles. As described in more detail below, the core comprises a benefit agent, and a partitioning modifier, and the shell comprises certain polymeric material. As described in more detail below, the core may include a benefit agent and optionally a partitioning modifier, and the shell may comprise certain polymers, namely an acrylate material.

The benefit agent delivery particles have a volume weighted median particle size of from about 30 microns to about 50 microns, preferably from about 30 to about 40 microns.

The populations of delivery particles can be combined with adjunct materials to form compositions. The composition may comprise from about 0.05% to about 20%, or from about 0.05% to about 10%, or from about 0.1% to about 5%, or from about 0.2% to about 2%, by weight of the composition, of delivery particles. The composition may comprise a sufficient amount of delivery particles to provide from about 0.05% to about 10%, or from about 0.1% to about 5%, or from about 0.1% to about 2%, by weight of the composition, of perfume to the composition. When discussing herein the amount or weight percentage of the delivery particles, it is meant the sum of the shell material and the core material.

The population of delivery particles may have a relatively wide distribution of particle sizes. As mentioned above it is believed that a wide distribution contributes to the compositions being more effective on certain surfaces such as various types of fabrics or garments. The population of delivery particles may be characterized by a Broadness Index, which is a way of characterizing the size distribution.

The Broadness Index is calculated by determining the particle size at which 90% of the cumulative particle volume is exceeded (90% size), the particle size at which 5% of the cumulative particle volume is exceeded (5% size), and the median volume-weighted particle size (50% size; where 50% of the particle volume is both above and below this size). The values can be used in the following equation to determine the Broadness Index for a population of delivery particles.

Broadness Index=(90% size–5% size)/50% size

The population of delivery particles of the present disclosure may be characterized by a Broadness Index of at least 1.0, preferably at least 1.1, more preferably at least 1.2. The population of delivery particles may be characterized by a Broadness Index of from about 1.0 to about 2.0, or from about 1.0 to about 1.8, or from about 1.1 to about 1.6, or from about 1.1 to about 1.5, or from about 1.2 to about 1.5, or from about 1.2 to about 1.4. Relatively higher Broadness Index values indicate a relatively wider particle size distribution.

The population of delivery particles may be characterized by one or more of the following: (i) a 5th-percentile volume-weighted particle size of from about 1 micron to about 15 microns; (ii) a 50th-percentile (median) volume-weighted particle size of from about 30 microns to about 50 microns; (iii) a 90th-percentile volume-weighted particle size of from about 40 microns to about 80 microns; or (iv) a combination thereof.

The delivery particles may be characterized by a fracture strength. Fracture strength is determined according to the procedure provided in the Test Method section below. The population of delivery particles may be characterized by an average Fracture Strength (where fracture strength is measured across several capsules at the median/d50 size of the population) of about 0.2 MPa to about 30 MPa, or about 0.4 MPa to about 10 MPa, or about 0.6 MPa to about 5 MPa, or even from about 0.8 MPa to about 4 MPa. The population of delivery particles may be characterized by an average Fracture Strength of about 0.2 MPa to about 10 MPa, or from about 0.5 MPa to about 8 MPa, or from about 0.5 MPa to about 6 MPa, or from about 0.5 MPa to about 5 MPa, or from about 0.7 MPa to about 4 MPa, or from about 1 MPa to about 3 MPa. The population of delivery particles may be characterized by an average Fracture Strength of from about 0.2 to about 10 MPa, preferably from about 0.5 to about 8 MPa, more preferably from about 0.5 to about 5 MPa. It is believed that delivery particles having an average Fracture Strength at d50 at these levels will perform well at one or more touchpoints that are typical for a surface, such as a fabric, treated with a composition according to the present disclosure.

Particular ratios of core material to shell material can result in populations of delivery particles that show improved performance. Without wishing to be bound by theory, it is believed that formulating delivery particles having a relatively high ratio of core to wall provides populations that have the desirable fracture strength profiles described in the present disclosure. Additionally, delivery particles with a high core:wall ratio can deliver a benefit agent more efficiently, requiring less wall material to deliver the same amount of benefit agent. Further, because the delivery particles have relatively high loading of benefit agent, less delivery particle material may be required for a particular composition, saving cost and/or freeing up formulation space.

The delivery particles of the present disclosure may be characterized by a core-to-polymer-wall weight ratio (also "core:polymer wall ratio," "core-wall ratio," "core:wall ratio," or even "C:W ratio" and the like, as used herein). Relatively high core:wall ratios are typically preferred to increase the delivery efficiency or relatively payload of the particles. However, if the ratio is too high, then the capsule may become too brittle or leaky and provide suboptimal performance.

As used herein, the core:polymer wall ratio is be understood as calculated on the basis of the weight of the reacted wall-forming materials and initiators that constitute the polymer wall, and for purposes of the calculation excludes in the calculation entrapped nonstructural materials, such as entrapped emulsifier. The calculation is based the amounts of the starting inputs, namely the input monomers and initiators. A sample core:wall polymer ratio calculation is illustrated in Example 1 below. If the amounts of starting inputs are not readily available, then the core:wall ratio is determined according to the Analytical Determination of the Core:Wall Ratio procedure provided in the Test Methods section.

A delivery particle, preferably the population of delivery particles, may be characterized by a core:polymer wall weight ratio of at least about 96:4, more preferably at least about 97:3, even more preferably at least about 98:2, even more preferably at least about 99:1. A delivery particle, preferably the population of delivery particles, may be characterized by a core-to-polymer-wall weight ratio of from about 96:4 to about 99.5:0.5, preferably from about 96:4 to about 99:1, more preferably from about 97:3 to about 99:1, even more preferably from about 98:2 to about 99:1. The core-to-polymer-wall weight ratio may be from about 96:4 to about 99:1, or from about 96:4 to about 98:2, or from about 97:3 to about 98:2.

Polymer Wall

The delivery particles of the present disclosure include a polymer wall that surrounds a core. The polymer wall comprises a polymeric material, specifically a (meth)acrylate polymer. The (meth)acrylate polymer is derived, at least in part, from one or more oil-soluble or oil-dispersible multifunctional (meth)acrylate monomers or oligomers.

The one or more oil-soluble or oil-dispersible multifunctional (meth)acrylate monomers or oligomers comprise at least three, preferably at least four, preferably at least five, preferably at least six, radical polymerizable functional groups. The one or more oil-soluble or oil-dispersible multifunctional (meth)acrylate monomers or oligomers may comprise from three to six, preferably from four to six, more preferably from five to six, most preferably six, radical polymerizable functional groups. It is believed that monomers comprising a relatively greater number of radical polymerizable groups result in, for example, delivery particles having preferred properties, such as less leakage, compared to monomers that have fewer radical polymerizable groups.

The radical polymerizable functional groups are independently selected from the group consisting of acrylate, methacrylate, styrene, allyl, vinyl, glycidyl, ether, epoxy, carboxyl, or hydroxyl, with the proviso that at least one of the radical polymerizable groups is acrylate or methacrylate. Preferably, the radical polymerizable functional groups are each independently selected from the group consisting of acrylate and methacrylate. It is believed that these functional groups result in delivery particles having preferred properties, such as less leakage, compared to other functional groups.

The polymer wall may comprise from about 5% to about 100%, preferably from about 40% to about 100%, more preferably from about 50% to about 100%, more preferably from about 75% to about 100%, more preferably from about 85% to about 100%, more preferably from about 90% to about 100%, even more preferably from about 95% to about 100%, by weight of the polymer wall, of the (meth)acrylate polymer. The polymer wall may comprise from about 5% to about 100%, preferably from about 40% to about 100%, more preferably from about 50% to about 100%, more preferably from about 75% to about 100%, more preferably from about 85% to about 100%, more preferably from about 90% to about 100%, even more preferably from about 95% to about 100%, by weight of the polymer wall, of the oil-soluble or oil-dispersible multifunctional (meth)acrylate monomer or oligomer. The (meth)acrylate polymer may comprise from about 5% to about 100%, preferably from about 40% to about 100%, more preferably from about 50% to about 100%, more preferably from about 75% to about 100%, more preferably from about 85% to about 100%, more preferably from about 90% to about 100%, even more preferably from about 95% to about 100%, by weight of the (meth)acrylate polymer, of the oil-soluble or oil-dispersible multifunctional (meth)acrylate monomer or oligomer.

The oil-soluble or oil-dispersible multifunctional (meth)acrylate monomers or oligomers may comprise a multifunctional aromatic urethane acrylate. Preferably, the oil-soluble or oil-dispersible multifunctional (meth)acrylate monomers or oligomers comprises a tri-, tetra-, penta-, or hexafunctional aromatic urethane acrylate.

Additionally, or alternatively, the oil-soluble or oil-dispersible multifunctional (meth)acrylate monomers or oligomers may comprise a multifunctional aliphatic urethane acrylate.

The (meth)acrylate polymer of the polymer wall may be derived from at least two different multifunctional (meth)acrylate monomers, for example first and second multifunctional (meth)acrylate monomers, each of which may preferably be oil-soluble or oil-dispersible. The first multifunctional (meth)acrylate monomer may comprise a different number of radical polymerizable functional groups compared to the second multifunctional (meth)acrylate monomer. For example, the first multifunctional (meth)acrylate monomer may comprise six radical polymerizable functional groups (e.g., hexafunctional), and the second multifunctional (meth)acrylate monomer may comprise less than six radical polymerizable functional groups, such as a number selected from three (e.g., trifunctional), four (e.g., tetrafunctional), or five (e.g., pentafunctional), preferably five. The first and second multifunctional (meth)acrylate monomers may be comprised of the same number of radical polymerizable functional groups, such as six (e.g., both monomers are hexafunctional), although the respective monomers are characterized by different structures or chemistries.

The oil-soluble or oil-dispersible (meth)acrylate may further comprise a monomer selected from an amine methacrylate, an acidic methacrylate, or a combination thereof.

The (meth)acrylate polymer of the polymer wall may be a reaction product derived from the oil-soluble or oil-dispersible multifunctional (meth)acrylate, a second monomer, and a third monomer. Preferably, the second monomer comprises a basic (meth)acrylate monomer, and the third monomer comprises an acidic (meth)acrylate monomer. The basic (meth)acrylate monomer or oligomer may be present at less than 2% by weight of the wall polymer. The acidic (meth)acrylate monomer or oligomer may be present at less than 2% by weight of the wall polymer.

The basic (meth)acrylate monomer, and/or oligomer or prepolymers thereof, may comprise one or more of an amine modified methacrylate, amine modified acrylate, a monomer such as mono or diacrylate amine, mono or dimethacrylate amine, amine modified polyether acrylate, amine modified polyether methacrylate, aminoalkyl acrylate, or aminoalkyl methacrylate. The amines can be primary, secondary or tertiary amines. Preferably the alkyl moieties of the basic (meth)acrylate monomer are C1 to C12.

Suitable amine (meth)acrylates for use in the particles of the present disclosure may include aminoalkyl acrylate or aminoalkyl methacrylate including, for example, but not by way of limitation, ethylaminoethyl acrylate, ethylaminoethyl methacrylate, aminoethyl acrylate, aminoethyl methacrylate, tertiarybutyl ethylamino acrylate, tertiarybutyl ethylamino methacrylate, tertiarybutyl aminoethyl acrylate, tertiarybutyl aminoethyl methacrylate, diethylamino acrylate, diethylamino methacrylate, diethylaminoethyl acrylate diethylaminoethyl methacrylate, dimethylaminoethyl acrylate and dimethylaminoethyl methacrylate. Preferably, the amine (meth)acrylate is aminoethyl acrylate or aminoethyl methacrylate, or tertiarybutyl aminoethyl methacrylate.

The acidic (meth)acrylate may comprise, by way of illustration, one or more of carboxy substituted acrylates or methacrylates, preferably carboxy substituted alkyl acrylates or methacrylates, such as carboxyalkyl acrylate, carboxyalkyl methacrylate, carboxyaryl acrylate, carboxy aryl methacrylate, and preferably the alky moieties are straight chain or branched C1 to C10. The carboxyl moiety can be bonded to any carbon of the C1 to C10 alkyl moiety, preferably a terminal carbon. Carboxy substituted aryl acrylates or methacrylates can also be used, or even (meth) acryloyloxyphenylalkylcarboxy acids. The alkyl moieties of the (meth)acryloyloxyphenylalkylcarboxy acids can be C1 to C10.

Suitable carboxy (meth)acrylates for use in particles of the present disclosure may include 2-carboxyethyl acrylate, 2-carboxyethyl methacrylate, 2-carboxypropyl acrylate, 2-carboxypropyl methacrylate, carboxyoctyl acrylate, carboxyoctyl methacrylate. Carboxy substituted aryl acrylates or methacrylates may include 2-acryloyloxybenzoic acid, 3-acryloyloxybenzoic acid, 4-acryloyloxybenzoic acid, 2-methacryloyloxybenzoic acid, 3-methacryloyloxybenzoic acid, and 4-methacryloyloxybenzoic acid. (Meth)acryloyloxyphenylalkylcarboxy acids by way of illustration and not limitation can include 4-acryloyloxyphenylacetic acid or 4-methacryloyloxyphenylacetic acid.

In addition to the oil-soluble or oil-dispersible multifunctional (meth)acrylate monomer or oligomer, the (meth) acrylate polymer of the polymer wall may be further derived from a water-soluble or water-dispersible mono- or multifunctional (meth)acrylate monomer or oligomer, which may include a hydrophilic functional group. The water-soluble or water-dispersible mono- or multifunctional (meth)acrylate monomer or oligomer may be preferably selected from the group consisting of amine (meth)acrylates, acidic (meth) acrylates, polyethylene glycol di(meth)acrylates, ethoxylated monofunctional (meth)acrylates, ethoxylated multifunctional (meth)acrylates, other (meth)acrylate monomers, other (meth)acrylate oligomers, and mixtures thereof.

When making the delivery particle, optionally emulsifier may be included, preferably in the water phase. The emulsifier may be a polymeric emulsifier. Emulsifier can help with further stabilizing the emulsion. In formation of the polymer wall of the delivery particle, the polymeric emulsifier can become entrapped in the polymer wall material. These inclusions of emulsifier into the polymer wall usefully can be used to advantage in modification of polymer wall properties, influencing such attributes as flexibility, leakage, strength, and other properties. Thus, the polymer wall of the delivery particles may further comprise a polymeric emulsifier entrapped in the polymer wall, preferably wherein the polymeric emulsifier comprises polyvinyl alcohol. As indicated above, however, the entrapped polymeric emulsifier is not to be included when determining the core:wall polymer weight ratio.

The benefit agent delivery particle, based on total benefit agent delivery particle weight, may comprise from about 0.5% to about 40%, preferably from about 0.5% to about 20%, more preferably 0.8% to 5% of an emulsifier, based on the weight of the wall material. Preferably, the emulsifier is selected from the group consisting of polyvinyl alcohol, carboxylated or partially hydrolyzed polyvinyl alcohol, methyl cellulose, hydroxyethylcellulose, carboxymethylcellulose, methylhydroxypropylcellulose, salts or esters of stearic acid, lecithin, organosulphonic acid, 2-acrylamido-2-alkylsulphonic acid, styrene sulphonic acid, polyvinylpyrrolidone, copolymers of N-vinylpyrrolidone, polyacrylic acid, polymethacrylic acid; copolymers of acrylic acid and methacrylic acid, and water-soluble surfactant polymers which lower the surface tension of water. The emulsifier preferably comprises polyvinyl alcohol, and the polyvinyl alcohol preferably has a hydrolysis degree from about 55% to about 99%, preferably from about 75% to about 95%, more preferably from about 85% to about 90% and most preferably from about 87% to about 89%. The polyvinyl alcohol may have a viscosity of from about 40 cps to about 80 cps, preferably from about 45 cps to about 72 cps, more preferably from about 45 cps to about 60 cps and most preferably 45 cps to 55 cps in an aqueous 4% polyvinyl alcohol solution at 20° C.; the viscosity of a polymer is determined by measuring a freshly made solution using a Brookfield LV type viscometer with UL adapter as described in British Standard EN ISO 15023-2:2006 Annex E Brookfield Test method. The polyvinyl alcohol may have a degree of polymerization of from about 1500 to about 2500, preferably from about 1600 to about 2200, more preferably from about 1600 to about 1900 and most preferably from about 1600 to about 1800. The weight average molecular weight of the polyvinyl alcohol may be of from about 130,000 to about 204,000 Daltons, preferably from about 146,000 to about 186,000, more preferably from about 146,000 to about 160,000, and most preferably from about 146,000 to about 155,000, and/or has a number average molecular weight of from about 65,000 to about 110,000 Daltons, preferably from about 70,000 to about 101,000, more preferably from about 70,000 to about 90,000 and most preferably from about 70,000 to about 80,000.

The (meth)acrylate polymer of the polymer wall may be further derived, at least in part, from at least one, and preferably one or more, oil-soluble or oil-dispersible and/or water-soluble or water-dispersible free radical initiators. One or more free radical initiators can provide a source of free radicals upon activation.

Without wishing to be bound by theory, it is believed that selecting the appropriate amount of initiator relative to total wall material (and/or wall monomers/oligomers) can result in improved capsules. For example, it is believed that levels of initiators that are too low may lead to poor polymer wall formation; levels that are too high may lead to encapsulate walls that have relatively low levels of structural monomers. In either situation, the resulting capsules may be relatively leaky and/or weak. It is further believed that the optimization of encapsulate wall formation, aided by proper selection of relative initiator level, is particularly important for capsules having relatively high core:wall ratios, given that the amount of wall material is relatively low.

Thus, the amount of initiator present may be from about 2% to about 50%, preferably from about 5% to about 40%, more preferably from about 10% to about 40%, even more preferably from about 15% to about 40%, even more preferably from about 20% to about 35%, or more preferably from about 20% to about 30%, by weight of the polymer wall (e.g., wall monomers plus initiators, excluding embedded polymeric emulsifiers, as described herein for core:wall ratios). It is believed that relatively higher amounts of initiator within the disclosed ranges may lead to improved, less-leaky capsules. The optimal amount of initiator may vary according to the nature of the core material. The (meth)acrylate polymer of the polymer wall may be derived from a first initiator and a second initiator, wherein the first and second initiators are present in a weight ratio of from about 5:1 to about 1:5, or preferably from about 3:1 to about 1:3, or more preferably from about 2:1 to about 1:2, or even more preferably from about 1.5:1 to about 1:1.5.

Suitable free radical initiators may include peroxy initiators, azo initiators, peroxides, and compounds such as 2,2'-azobismethylbutyronitrile, dibenzoyl peroxide. More particularly, and without limitation, the free radical initiator can be selected from the group of initiators comprising an azo or peroxy initiator, such as peroxide, dialkyl peroxide, alkylperoxide, peroxyester, peroxycarbonate, peroxyketone and peroxydicarbonate, 2,2'-azobis (isobutylnitrile), 2,2'-azobis (2,4-dimethylpentanenitrile), 2,2'-azobis (2,4-dimethylvaleronitrile), 2,2'-azobis(2-methylpropanenitrile), 2,2'-azobis (2-methylbutyronitrile), 1,1'-azobis (cyclohexanecarbonitrile), 1,1'-azobis(cyanocyclohexane), benzoyl peroxide, decanoyl peroxide; lauroyl peroxide; benzoyl peroxide, di(n-propyl)peroxydicarbonate, di(sec-butyl) peroxydicarbonate, di(2-ethylhexyl)peroxydicarbonate, 1,1-dimethyl-3-hydroxybutyl peroxyneodecanoate, a-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di (2-ethylhexanoyl peroxy) hexane, t-amyl peroxy-2-ethylhexanoate, t-butyl peroxy-2-ethylhexanoate, t-butyl peroxyacetate, di-t-amyl peroxyacetate, t-butyl peroxide, di-t-amyl peroxide, 2,5-dimethyl-2,5-di-(t-butylperoxy)hexyne-3, cumene hyderoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate, ethyl 3,3-di-(t-amylperoxy)-butyrate, and the like.

The shell of the delivery particles may comprise a coating, for example on an outer surface of the shell, away from the core. The encapsulates may be manufactured and be subsequently coated with a coating material. The coating may be useful as a deposition aid. The coating may comprise a cationic material, such as a cationic polymer. As indicated above, however, a coating that is not a structural or support feature of the wall is not to be included in calculations when determining the core:wall polymer weight ratio.

The particles of the present disclosure include a shell, or polymer wall, the terms being synonymous. The shell may comprise certain polymers, which may be reaction products of certain monomers. The polymer wall is the reaction product of one or more multifunctional (meth)acrylate monomers of one or more oil phases wherein the one or more oil-soluble or dispersible multifunctional (meth)acrylate monomers or oligomers have at least three, and preferably at least four, radical polymerizable functional groups wherein the radical polymerizable functional groups are each independently selected from acrylate, methacrylate, styrene, allyl, vinyl, glycidyl, ether, epoxy, carboxyl, or hydroxyl, with the proviso that at least one of the radical polymerizable groups is acrylate or methacrylate. The polymer wall in addition or in combination with the monomers of the oil phase can also optionally be further derived from the reaction product one or more mono- and/or multifunctional methacrylate monomers from at least one water phase.

The invention can be practiced in various embodiments. For example, in one embodiment the delivery particle herein comprises a core and a polymer wall encapsulating said core, wherein the core comprises an oily medium comprising a benefit agent and a partitioning modifier. In such embodiment, the partitioning modifier comprises from 5 to 55% by weight of the core. The polymer wall comprises a (meth)acrylate polymer derived, at least in part, from one or more oil-soluble or dispersible multifunctional (meth)acrylate monomers or oligomers. The one or more oil-soluble or dispersible multifunctional (meth)acrylate monomers or oligomers have at least three radical polymerizable functional groups. The radical polymerizable functional groups can be independently selected from acrylate, methacrylate, styrene, allyl, vinyl, glycidyl ether, epoxy, carboxyl, or hydroxyl. At least one of the radical polymerizable groups should be acrylate or methacrylate.

The delivery particle has a core to polymer wall ratio by weight from about 96:4 to about 99.5 to 0.5, or even about 98:2 to about 99:1 and the delivery particle has a volume-weighted particle size from about 30 to about 50 microns.

Optionally, the polymer wall is also the reaction product of at least one water soluble or dispersible mono- or multi-functional (meth)acrylate monomer and/or oligomer. Free radical initiators in the oil or water phases or both, are optional, but preferable, to promote polymerization of the monomers in each respective phase.

In a further embodiment, the water soluble or dispersible multifunctional (meth)acrylate monomer or oligomer is a multifunctional aromatic urethane acrylate. An illustrative example is a hexafunctional aromatic urethane acrylate.

In a further embodiment, the oil soluble or dispersible multifunctional monomers or oligomers comprise in addition one or more multifunctional aliphatic urethane acrylates. In a further embodiment the oil soluble or dispersible (meth)acrylate includes in addition one or more of an amine methacrylate or an acidic methacrylate.

In another embodiment the aqueous phase wall forming composition comprises one or more water soluble (meth)acrylate monomers or oligomers having a hydrophilic functional group.

In a further embodiment, a water soluble or dispersible mono- or multi-functional (meth)acrylate monomer and/or oligomer can be used in addition and comprises one or more amine methacrylates, acidic methacrylates, polyethylene glycol di(meth)acrylates, ethoxylated mono- or multi-functional (meth)acrylates, and (meth)acrylate monomers and/or oligomers.

In an embodiment, the core of the delivery particle is a benefit agent comprising a fragrance. Usefully, the fragrance is a perfume accord comprising one or more perfumes having a log P of from 2.5 to 4. The core can comprise at least one partitioning modifier, selected from the group consisting of isopropyl myristate, vegetable oil, modified vegetable oil, mono-, di-, and tri-esters of C4-C24 fatty acids, propan-2-yl tetradecanoate, isopropyl myristate, dodecanophenone, lauryl laurate, methyl behenate, methyl laurate, methyl palmitate, methyl stearate, and mixtures thereof.

Optionally, emulsifier can be included in the water phase. Emulsifier can help with further stabilizing the emulsion. In formation of the polymer wall of the microcapsule the polymeric emulsifier can become entrapped in the polymer wall material. These inclusions of emulsifier into the polymer wall usefully can be used to advantage in modification of polymer wall properties, influencing such attributes as flexibility, leakage, strength, and other properties.

Surprisingly in the invention, the delivery particle for a constant core to polymer wall ratio, the leakage of the delivery particle decreases as size of the delivery particle increases, within the range of from 30 to 50 um.

Core to polymer wall ratio is be understood as calculated on the basis of the weight of the reacted wall forming materials and initiators that constitute the polymer wall, and for purposes of the calculation excludes in the calculation entrapped nonstructural materials such as entrapped emulsifier. The calculation is on the basis of the starting inputs, namely the input monomers and initiators.

The core comprises a benefit agent and a partitioning modifier wherein the partitioning modifier comprises from 5% to 55% by weight of the core. The partitioning modifier is selected from the group consisting of isopropyl myristate, vegetable oil, modified vegetable oil, mono-, di-, and tri-esters of C4-C24 fatty acids, propan-2-yl tetradecanoate, dodecanophenone, lauryl laurate, methyl behenate, methyl laurate, methyl palmitate, methyl stearate, and mixtures thereof, preferably the partitioning modifier is isopropyl myristate. In one embodiment, the core comprises a benefit agent and isopropyl myristate. In an alternate embodiment, if desired a second partitioning modifier is included, in addition to the first partitioning modifier, the second partitioning modifier in the benefit agent delivery particle comprises, based on total core weight, from about 0% to about 80%, preferably 0% to 50%, more preferably from about 0% to about 30%, most preferably 20% or less of the one or more additional partitioning modifiers. In the preferred embodiment, isopropyl myristate is the partitioning modifier and a second partitioning modifier is not used.

For ease of calculation, to achieve 5 to 55% partitioning modifier by weight of the core in the process of making, the wet inputs of the core can be ascertained on the basis of the percent of the wet slurry. By way of illustration, when the core is comprised of 5% IPM and 95% perfume, that 5% of the partitioning modifier, e.g., IPM, corresponds to 1.97% of the slurry (therefore approximately 2%). When the core is comprised of 55% IPM and 45% perfume, that 55% of IPM represents 21.69% of the slurry (therefore approximately 22%). % slurry, it is to be understood as wet %.

In another aspect, the invention teaches a composition comprising benefit agent delivery particles, having a volume weighted median particle size from about 30 to about 50 microns.

An optional second monomer, and/or oligomer or prepolymers thereof, may comprise a basic (meth)acrylate monomer and an optional third monomer may comprise an acidic (meth)acrylate monomer.

The basic (meth)acrylate monomer or oligomer may be present at less than 1% by weight of the benefit agent delivery particle. The acidic (meth)acrylate monomer or oligomer may be present at less than 1% by weight of the benefit agent delivery particle.

The described composition benefit agent delivery particles desirably have a one-week leakage percent of the core of less than 25% by weight, measured at 35° C.

Optionally, in the composition of the present disclosure, any of the first, and optional second and third monomers may be oligomers, monomers or prepolymers.

The benefit agent delivery particle, based on total benefit agent delivery particle weight, may comprise from about 0.5% to about 40%, more preferably 0.8% to 5% of an emulsifier. Preferably said emulsifier is selected from the group consisting of polyvinyl alcohol, carboxylated or partially hydrolyzed polyvinyl alcohol, methyl cellulose, hydroxyethylcellulose, carboxymethylcellulose, methylhydroxypropylcellulose, salts or esters of stearic acid, lecithin, organosulphonic acid, 2-acrylamido-2-alkylsulphonic acid, styrene sulphonic acid, polyvinylpyrrolidone, copolymers of N-vinylpyrrolidone, polyacrylic acid, polymethacrylic acid; copolymers of acrylic acid and methacrylic acid, and water-soluble surfactant polymers which lower the surface tension of water. The emulsifier preferably comprises polyvinyl alcohol, and said polyvinyl alcohol preferably has a hydrolysis degree from about 55% to about 99%, preferably from about 75% to about 95%, more preferably from about 85% to about 90% and most preferably from about 87% to about 89%. The polyvinyl alcohol may have a viscosity of from about 40 cps to about 80 cps, preferably from about 45 cps to about 72 cps, more preferably from about 45 cps to about 60 cps and most preferably 45 cps to 55 cps in 4% water solution at 20° C. The polyvinyl alcohol may have a degree of polymerization of from about 1500 to about 2500, preferably from about 1600 to about 2200, more preferably from about 1600 to about 1900 and most preferably from about 1600 to about 1800. The weight average molecular weight of the polyvinyl alcohol may be of from about 130,000 to about 204,000 Daltons, preferably from about 146,000 to about 186,000, more preferably from about 146,000 to about 160,000, and most preferably from about 146,000 to about 155,000, and/or has a number average molecular weight of from about 65,000 to about 110,000 Daltons, preferably from about 70,000 to about 101,000, more preferably from about 70,000 to about 90,000 and most preferably from about 70,000 to about 80,000.

The benefit agent delivery particles of the present disclosure may comprise a coating. The shell of the delivery particles may comprise a coating, for example on an outer surface of the shell, away from the core. The coating may comprise a cationic material, such as a cationic polymer. As indicated above, however, a coating that is not a structural or support feature of the wall is not to be included in calculations when determining the core:wall polymer weight ratio. The particles may be manufactured and be subsequently coated with a coating material. The coating may be useful as a deposition aid. Non-limiting examples of coating materials include but are not limited to materials selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone and its co polymers, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines and copolymers of polyvinyl amines, polyvinyl formamides, and polyallyl amines and mixtures thereof. The coating material may be a cationic polymer.

Benefit Agent

The particles of the present disclosure include a core that comprises a benefit agent. Suitable benefit agents located in the core may include benefit agents that provide benefits to a surface, such as a fabric or hair.

The benefit agent may be selected from the group consisting of perfume raw materials, lubricants, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, agricultural actives, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents, sun fade inhibitors, anti-allergenic agents, enzymes, water proofing agents, fabric comfort agents, shrinkage resistance agents, stretch resistance agents, stretch recovery agents, skin care agents, glycerin, synthetic or natural actives, antibacterial actives, antiperspirant actives, cationic polymers, dyes and mixtures thereof.

The encapsulated benefit agent may include perfume raw materials. The term "perfume raw material" (or "PRM") as used herein refers to compounds having a molecular weight of at least about 100 g/mol and which are useful in imparting an odor, fragrance, essence or scent, either alone or with other perfume raw materials. Typical PRMs comprise inter alia alcohols, ketones, aldehydes, esters, ethers, nitrites and alkenes, such as terpene. A listing of common PRMs can be found in various reference sources, for example, "Perfume and Flavor Chemicals", Vols. I and II; Steffen Arctander Allured Pub. Co. (1994) and "Perfumes: Art, Science and Technology", Miller, P. M. and Lamparsky, D., Blackie Academic and Professional (1994).

The PRMs may be characterized by their boiling points (B.P.) measured at the normal pressure (760 mm Hg), and their octanol/water partitioning coefficient (P), which may be described in terms of log P, determined according to the test method below. Based on these characteristics, the PRMs may be categorized as Quadrant I, Quadrant II, Quadrant III, or Quadrant IV perfumes, as described in more detail below.

The perfume raw materials may comprise a perfume raw material selected from the group consisting of perfume raw materials having a boiling point (B.P.) lower than about 250° C. and a ClogP from 2.5 to 4, or even lower than about 3, perfume raw materials having a B.P. of greater than about 250° C. and a ClogP of greater than about 3, perfume raw materials having a B.P. of greater than about 250° C. and a ClogP lower than about 3, perfume raw materials having a B.P. lower than about 250° C. and a ClogP greater than about 3 and mixtures thereof. Perfume raw materials having a boiling point B.P. lower than about 250° C. and a ClogP lower than about 3 are known as Quadrant I perfume raw materials. Quadrant 1 perfume raw materials are preferably limited to less than 30% of the perfume composition. Perfume raw materials having a B.P. of greater than about 250° C. and a ClogP of greater than about 3 are known as Quadrant IV perfume raw materials, perfume raw materials having a B.P. of greater than about 250° C. and a ClogP lower than about 3 are known as Quadrant II perfume raw materials, perfume raw materials having a B.P. lower than about 250° C. and a ClogP greater than about 3 are known as a Quadrant III perfume raw materials. Suitable Quadrant I, II, III and IV perfume raw materials are disclosed in U.S. Pat. No. 6,869,923 B1.

The benefit agent itself, for example perfume oil, can function as the oil phase or oily medium for dissolution or dispersal of oil phase monomers and the partition modifier. Optionally an organic oil, or more particularly a nonsolvent for the water phase can be employed as the oily medium or oil phase.

Internal phase oils, or oil phase, or solvent or organic solvents, or "nonsolvent for the water phase," are used interchangeably for purposes hereof. Benefit agent can itself be an oil. Perfume can itself be such an oil. Illustrative of such perfume oil is when the benefit agent is selected to be an essential oil. In most instances additional oil phase becomes optional. Typical organic oils can optionally be employed together with the benefit agent such as perfume oil, are typically a nonsolvent for the water phase, and are used in an amount sufficient for facilitating dissolving or dispersing the desired benefit agent such as perfume oil, and may include various solvents such as vegetable oils, esterified oils, essential oils, mono-propylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, 3-methoxy-3-methyl-butanol, alkanediols, propylene glycols, various alcohols, and blends of any of the foregoing.

The oily medium in addition to benefit agent, can comprise oils selected to be somewhat or substantially water insoluble or water insoluble to a degree or able to be made substantially water insoluble at certain pH's. The purpose of the oily medium is to facilitate emulsifying step or solubilizing or dispersing the desired benefit agent. Other useful optional oil phase oils include vegetable oils such as canola oil, soybean oil, corn oil, cottonseed oil, alkyl esters of fatty acids, transesterified vegetable oils such as transesterified canola oil, soybean oil, corn oil, cottonseed oil, sunflower oil, methyl ester of oleic acid, parafinnic aliphatic hydrocarbons The oil phase in the encapsulation process can be benefit agent, but can be any material which is liquid within the temperature range at which the capsules are formed. Examples of eligible various conventional organic oils for use with different benefit agents can include ethyldiphenylmethane, benzylxylene, alkyl biphenyls such as propylbiphenyl; butylbiphenyl, dialkyl phthalates, dodecyl benzene; alkyl or aralkyl benzoates such as benzyl benzoate; alkylated naphthalenes such as dipropylnaphthalene; partially hydrogenated terphenyls; high-boiling straight or branched chain hydrocarbons; and mixtures of the above.

In an alternate aspect the perfume core material can be a fraction of the microcapsule core or 100 weight percent of the core. When the perfume core material is itself an organic liquid, additional diluent oil can be optional depending on the desired amount of fragrance sought to be delivered by the delivery system of the invention.

Partitioning Modifier

The core of the benefit agent delivery particles of the present disclosure comprises an oily medium such as benefit agent, and/or an oil solvent for the benefit agent, and a partitioning modifier. The benefit agent itself, if liquid or liquifiable or an oil, solubilizes the oil phase monomers. The core of the benefit agent particle may comprise a partitioning modifier. The properties of the oily medium in the core can play a role in determining how much, how quickly, and/or how permeable the polyacrylate shell material will be when established at the oil/water interface. For example, if the oil phase comprises highly polar materials, these materials may reduce the diffusion of the acrylate oligomers and polymers to the oil/water interface and result in a very thin, highly permeable shell. Incorporation of a partitioning modifier can adjust the polarity of the core, thereby changing the partition coefficient of the polar materials in the partitioning modifier versus the acrylate oligomers, and can result in the establishment of a well-defined, highly impermeable shell. The partitioning modifier may be combined with the core's perfume oil material prior to incorporation of the wall-forming monomers.

The partitioning modifier may be present in the core at a level of from about 5% to about 55%, preferably from about 10% to about 50%, more preferably from about 25% to about 50%, by weight of the core.

The partitioning modifier may comprise a material selected from the group consisting of vegetable oil, modified vegetable oil, mono-, di- and tri-esters of $C_4C_{24}$ fatty acids, isopropyl myristate, dodecanophenone, lauryl laurate, methyl behenate, methyl laurate, methyl palmitate, methyl stearate, and mixtures thereof. The partitioning modifier may preferably comprise or even consist of isopropyl myristate. The modified vegetable oil may be esterified and/or brominated. The modified vegetable oil may preferably comprise castor oil and/or soybean oil. US Patent Application Publication 20110268802, incorporated herein by reference, describes other partitioning modifiers that may be useful in the presently described delivery particles.

Emulsifiers

Optionally, the encapsulates and/or compositions comprising the encapsulates may comprise emulsifiers (for example, in addition to the polyvinyl alcohol disclosed above), which may be useful in the formation of the encapsulates. Additional emulsifiers may include by way of illustration and not limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly (styrene sulfonate) sodium salt, alkylene-maleic anhydride copolymers such as isobutylene-maleic anhydride copolymer, or ethylene maleic anhydride copolymer gum arabic, sodium alginate, carboxymethylcellulose, cellulose sulfate and pectin, poly(styrene sulfonate), pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; maleic anhydride copolymers (including hydrolyzates thereof), polyacrylic acid, polymethacrylic acid, acrylic acid alkyl acrylate copolymers such as acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates. The amount of emulsifier can be selected anywhere from about 0.1 to about 40 percent by weight of all constituents, in one aspect from 0.5 to about 10 percent, in another aspect from 0.5 to 5 percent by weight. In another aspect emulsifier is employed at 0.2 to about 10% by weight based on percentage of the total formulation.

Method of Making Benefit Agent Delivery Particles

A process of making a delivery particle comprising a core and a polymer wall encapsulating said core is disclosed, wherein the core comprises an oily medium comprising a benefit agent. For example, particles may be made by a process that comprises heating, in one or more heating steps, an emulsion, the emulsion produced by dissolving or dispersing into a water phase, optionally, a water soluble or dispersible initiator and optionally at least one mono- or multi-functional (meth)acrylate monomer and/or oligomer wherein the free radical initiator is used at an amount from 0% to 5% by weight. Initiator is typically used at from 0% to 5% by weight of the respective phase to which the initiator is added.

The emulsion is formed of an oil phase dispersed into the water phase. Dissolved or dispersed into the oil phase is the core which is an oily medium comprising the benefit agent, optionally solvent, and the partitioning modifier. Dissolved or dispersed into the oil phase is also one or more oil-soluble or dispersible multifunctional (meth)acrylate monomers and/or oligomers having at least three, and preferably at least four, radical polymerizable functional groups wherein the radical polymerizable functional groups are selected from acrylate, methacrylate, styrene, allyl, vinyl, glycidyl ether, epoxy, carboxyl, or hydroxyl.

Optionally, but preferably, included in the water and/or oil phases is one or more of an acidic (meth)acrylate and/or an basic (meth)acrylate at a minor concentration of about less than about 5% by weight or even less than about 1% by weight, optimally at a range of from about 0.001% to about 5% by weight based on the weight of the polymer wall. Minor amounts of other monofunctional (meth)acrylates can also be included to adjust wall properties in specific applications.

Basic (meth)acrylate monomer and acid (meth)acrylate monomer typically are used in a molar proportion from 3:1 to 1:3 and together have a percent by weight as compared to the weight of the wall material of from 0 to 5%.

In general, the oil soluble multifunctional (meth)acrylate monomer is soluble or dispersible in the oil phase, typically soluble at least to the extent of 1 gram in 100 ml of the oil, or dispersible or emulsifiable therein. The water soluble multifunctional (meth)acrylate monomers are typically soluble or dispersible in water, typically soluble at least to the extent of 1 gram in 100 ml of water, or dispersible therein.

In the process of making the benefit agent delivery particles, assuming a slurry system of about 800 g including an oil phase and/or benefit agent being an oil, the largest constituents are typically the oil(s), with 10 to 70 weight percent, preferably 25 to 55 weight percent the benefit agent; 10 to 70 weight percent, preferably 35 to 65 weight percent water; preferably 0.1 to 10 weight percent, usually 0.5 to 8 weight percent multi-functional (meth)acrylate monomer; and additional oil, if any, 0 to 20 weight percent. Initiator is 10% or less, usually about 5% or less, preferably 2% by weight or less and more preferably 1% or less. Water phase mono- or multifunctional (meth)acrylate monomer is at 0.01 to 20 weight percent, preferably 0.025 to about 0.5 weight percent, more preferably 0.05 to 0.25% of the system. Second and third monomers such as acidic or basic (meth) acrylate monomer are each at 0.01 to 1 weight percent of the system.

The oil phase is emulsified into the water phase under high shear agitation to form the oil in water emulsion comprising droplets of the core and oil phase dispersed in the water phase. Encapsulates are formed by reacting the respective monomers and/or oligomers of the water and oil phases by heating the emulsion thereby forming a polymer wall comprising a (meth)acrylate polymer derived from the oil phase multifunctional(meth)acrylate monomers and/or oligomers, and the acidic methacrylate and/or basic methacrylate, which can facilitate driving polymer wall material to the interface. If included in the oil phase (meth)acrylate monomers and/or oligomers, The acidic and/or basic methacrylates are typically selected to be water soluble.

In the method of making microcapsules a dispersion is formed of the oil phase composition. The core's oily medium is hydrophobic. The multifunctional (meth)acrylate monomer is dissolved or dispersed in one or more oil phases and is emulsified into the water phase. The radical polymerizable groups of the multifunctional methacrylate, upon heating, facilitate self-polymerization of the multifunctional methacrylate. Optionally, an initiator is included.

The one or more oil phases comprises one or more oil soluble or dispersible multi-functional (meth)acrylate monomers or oligomers, and, optionally, through preferably, an initiator for effecting polymerization of the multi-functional (meth)acrylate monomers/oligomers, and one or more benefit agents, i.e., the ingredients or components intended to be encapsulated. For purposes hereof multi-functional (meth) acrylate is inclusive of di-functional (meth)acrylates.

The polymer wall can be a combination of from 5 to 100% by weight of one or more multifunctional (meth)acrylate of the oil phase and/or water phase; 0 to 5% of acid (meth) acrylate; 0 to 5% of basic (meth)acrylate; 0 to 5% of mono-functional (meth)acrylate.

The oil phase is combined with an excess of the water phase. Optionally, though preferably, the oil phase further comprises the initiator. If more than one oil phase is employed, these generally are first combined, and then combined with the water phase. The water phase is an aqueous composition comprising an emulsifier suitable for emulsifying the oil phase(s) composition in water and, optionally, includes an initiator. The combined phases are intimately mixed to form an emulsion of droplets of the combined oil phase composition dispersed in the aqueous phase. High shear agitation is applied to form droplets of a target size, which influences the final size of the finished encapsulates. If desired, the water phase can also comprise one or more water phases that are sequentially combined.

Heat is applied to the emulsion, or depending on the initiator selected, other conditions such as actinic radiation polymerize the multifunctional (meth)acrylate of the oil phase, and any added monomers or oligomers of either or both of the oil or water phases. Heating can generate free radicals by decomposing the initiator, if added.

The forming polymer generally forms at an interface of the oil phase and water phase materials, with or without applying or inducing conditions to cause the oligomer/prepolymer material to migrate to said interface, to initiate capsule wall formation at the interface. Where water soluble or dispersible acidic or basic (meth)acrylate monomers are included, the forming polymer tends to drive toward the interface or forms at the interface. Optionally, a second initiator can be included in the oil phase, as well, at from 0% to 5% by weight based on weight of the oil phase.

Reaction is continued for a time as necessary to attain the desired capsule wall thickness.

The oil phase monomers are able to self-polymerize. Preferably a water soluble initiator is included in the water phase facilitating polymerization of the oil phase monomers or oligomers and any water soluble or water dispersible (meth)acrylate at the oil water interface. Alternatively, the first water soluble initiator is a combination of initiators at least one of which is capable of initiating polymerization of oil phase multi-functional (meth)acrylate oligomer/prepolymer and/or any monomers in the water phase. Optionally at least one oil phase initiator can be included which is capable of initiating polymerization oil phase multi-functional (meth)acrylate oligomer/prepolymer. The skilled artisan will recognize that the monomers as has been defined in this specification, are understood and intended to encompass the various oligomers/prepolymers thereof, and that these may even be pre-formed and then employed in the practice of the present claimed methods. All such variations of monomers are intended encompassed. In one embodiment, the first step may comprise forming a first oil phase composition comprising the reaction product of at least one oil soluble or dispersible amine (meth)acrylate, at least one oil soluble or dispersible acidic (meth)acrylate, and at least one oil soluble or dispersible multifunctional (meth)acrylate monomer or oligomer, which reaction product is an oligomer and/or prepolymer which may be self-polymerizable or reacted at the oil water interface via an initiator in the water phase.

The aqueous phase composition is preferably added to the reaction mix after initiating polymerization of the oligomer/prepolymer to form the capsule wall but before completion thereof. More preferably, the aqueous phase composition is added shortly after initiation of the capsule wall formation, most preferably before the oil phase droplet has been fully encapsulated or has achieved a thickness whereby polymerization of the oil phase oligomer/prepolymer is fully isolated from the polymerization of the water soluble or dispersible (meth)acrylate unless the latter is co-polymerizable with the former.

Optionally, the water phase can include water soluble or water dispersible (meth)acrylates such as polyethylene glycol (meth)acrylates, ethoxylated mono- or multi-functional (meth)acrylates, and (meth)acrylate monomers and/or oligomers that are capable of being dispersed in water with a small amount of a suitable emulsifier or with elevated temperature or select pH. Monomers co-polymerizable with the multi-functional (meth)acrylates of the oil phase are preferred.

Depending upon the selection of the water soluble or dispersible (meth)acrylate and the timing of its addition, the water soluble or dispersible (meth)acrylate may copolymerize with and/or form an interpenetrating network with the multifunctional (meth)acrylate of the oil phase and/or the polymerized oligomer/prepolymer. Once the oil phase droplet is encapsulated, capsule wall formation continues until the desired end-point. Optionally reaction can be continued with the oil phase (meth)acrylate oligomer/prepolymer continuing to build from the inner surface of the capsule wall inwards and the water soluble or dispersible (meth)acrylate continuing to build and add to the exterior surface of the capsule wall. The wall surface is comprised of the polymerized oligomers/prepolymers of the oil phase polymerized with any water soluble or water dispersible (meth)acrylate monomers and/or oligomers of the water phase.

Oligomerization/pre-polymerization and polymerization are initiated by suitable initiators, most especially free radical initiators. Selection of the initiator is dependent, in part, upon the monomers, oligomers and/or prepolymers to be polymerized or further oligomerized as well as the method by which the initiator is activated: in the case of free radical initiators, the method by which the free radical is to be generated, e.g., heat, actinic radiation. Latent initiators are also contemplated where a first action, particularly a chemical reaction, is needed to transform the latent initiator into an active initiator which subsequently initiates polymerization upon exposure to polymerizing conditions. Where multiple initiators are present, it is contemplated, and preferred, that each initiator be initiated or suitably initiated by a different condition. For example, each initiator may be initiated by a different temperature or one may be induced by heat and the other by actinic radiation. Although certain heat activated initiators may be initiated by certain temperature trigger points, generally their activity is expressed in terms of their 10 hour half-life. In this respect, one initiator may have a 10 hour half-life at 60° C. and another at 80° C. With respect to actinic radiation activated initiators one may use initiators that are activated by different wavelengths and/or adjust the intensity of the light to alter the speed of polymerization of one polymerizable composition over another. Use of different initiators with different activation triggers allows for more control in the capsule wall formation. Depending upon the method of activation, control of oligomerization/pre-polymerization and/or wall formation may be accomplished by limiting the time and/or extent of activation, e.g., by exposing the specific reaction mix to sufficient temperatures or and/or actinic radiation for a limited period of time and/or by increasing the intensity of the activation energy, i.e. increasing the temperature and/or the intensity of the light.

By selection of monomers according to the invention and controlling relative proportions of the monomers and droplet size, a delivery particle having a core to polymer wall ratio by weight from about 96:4 to about 99.5 to 0.5, or even about 98:2 to about 99:1 is achieved. Advantageously the delivery particles have a particle size from 30 to 50 microns, a volume weighted fracture strength of from 0.2 to 10 MPa.

Surprisingly, in certain embodiments, the reacting step can be carried out in the substantial absence of initiator. The oil phase monomers or oligomers can be selected to be self-polymerizable. In one embodiment, the multifunctional (meth)acrylate monomer or oligomer of the oil phase is a multifunctional aromatic urethane acrylate such as a tri-, tetra-, penta-, or hexafunctional aromatic urethane acrylate, preferably hexafunctional aromatic urethane acrylate. The dissolving or dispersing step into the oil phase can comprise in addition dissolving or dispersing one or more multifunctional aliphatic urethane acrylates.

The dissolving or dispersing step into the oil phase oil can comprise in addition dissolving or dispersing one or more of an amine methacrylate or an acidic methacrylate, preferably both into the water phase and/or oil phase. The addition of amine methacrylate or an acidic methacrylate especially into the water phase facilitates polymerization of the respective monomers at an interface of the oil and water phases in the emulsion. Particularly preferred is dissolving or dispersing in addition into the water phase one or more amine methacrylates and acidic methacrylates, polyethylene glycol di(meth)acrylates, ethoxylated mono- or multi-functional (meth)acrylates, and (meth)acrylate monomers and/or oligomers.

In the process of the invention, although addition of emulsifier is optional, the additional step of adding a polymeric emulsifier to the water phase or during emulsifying facilitates formation of a stable emulsion. The polymeric emulsifier useful can modify properties of the polymer wall of the encapsulates by becoming entrapped or encased in the polymer wall.

For a constant core to polymer wall ratio, the leakage of the delivery particles according to the invention surprisingly was found to decrease as size of the delivery particle increases, within the range of from 30 to 50 um. Also, for a constant core to polymer wall ratio, the fracture strength of the delivery particle increases as size of the delivery particle increases, within the range of from 30 to 50 um.

The particles of the present disclosure may be made by a process that comprises heating, in one or more heating steps, the emulsion, the emulsion produced by emulsifying the combination of: a) an oil phase formed by combining a first oil, b) a multifunctional (meth)acrylate and c) a benefit agent, preferably a fragrance. Optionally a second oil can be employed as well. The oil phase comprises an initiator, and optionally a partitioning modifier, preferably the partitioning modifier comprises a material selected from the group consisting of vegetable oil, modified vegetable oil, propan-2-yl tetradecanoate, and preferably isopropyl myristate. Modified vegetable oil can be esterified and/or brominated, preferably the vegetable oil comprises castor oil and/or soybean oil.

An optional second oil can be employed and one or more of the following can be optionally dispersed or dissolved into the second oil, or if water soluble or dispersible, then dissolved or dispersed into a water phase:
(i) an aminoalkylacrylate and/or methacrylate monomer or oligomer;
(ii) a carboxy alkyl acrylate monomer and/or oligomer;
(iii) a material selected from the group consisting of a multifunctional acrylate monomer, multifunctional methacrylate monomer, multifunctional methacrylate oligomer, multifunctional acrylate oligomer and mixtures thereof;
(iv) a benefit agents such as a perfume.

The water phase as herein described can comprise, a pH adjuster, an emulsifier, preferably an anionic emulsifier, preferably the emulsifier comprises polyvinyl alcohol and optionally an initiator. Alternative to or in addition to the emulsifier, a surfactant can use used also to facilitate emulsification.

In the described process the heating step comprises heating the emulsion from about 1 hour to about 20 hours, preferably from about 2 hours to about 15 hours, more preferably about 4 hours to about 10 hours, most preferably from about 5 to about 7 hours sufficiently to transfer from about 500 joules/kg to about 5000 joules/kg to said emulsion, from about 1000 joules/kg to about 4500 joules/kg to said emulsion, from about 2900 joules/kg to about 4000 joules/kg to said emulsion.

Prior to the heating step, the emulsion has a volume weighted median particle size of the emulsion droplets of from about 0.5 microns to about 100 microns, even from about 1 microns to about 60 microns, or even from 20 to 50 microns, preferably from about 30 microns to about 50 microns, with a view to have a resulting finished encapsulated particle from about 30 to about 50 microns.

A slurry can be made of the benefit agent delivery particles made by the above process by combining with adjunct material including water or other fluid carrier. The population can also be employed in dry or cake form. One or more perfumes that are different from the perfume or perfumes contained in the core of the benefit agent delivery particles can be used external to the core-shell benefit agent delivery particles.

Delivery Particle Adjunct Material

The benefit agent delivery particle compositions of the present disclosure may comprise an adjunct material. The adjunct material may be a processing and/or stability aid such as in slurries of the population of benefit agent delivery particles. Similarly, adjuncts can be added to dry or dewatered forms of the population of benefit agent delivery particles.

Suitable adjunct materials may include: surfactants, conditioning actives, deposition aids, rheology modifiers or structurants, bleach systems, stabilizers, builders, chelating agents, dye transfer inhibiting agents, dye transfer enhancing agents, dispersants, enzymes, and enzyme stabilizers, catalytic metal complexes, polymeric dispersing agents, clay and soil removal/anti-redeposition agents, brighteners, suds suppressors, silicones, hueing agents, aesthetic dyes, additional perfumes and perfume delivery systems, structure elasticizing agents, carriers, additional benefit agents, hydrotropes, processing aids, structurants, anti-agglomeration agents, coatings, aldehyde scavengers, and/or pigments.

Depending on the intended form, formulation, and/or end-use, compositions of the present disclosure may or may not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments. The benefit agents suitable for being located in the core of the particles or microcapsules, as described above, may additionally or alternatively be suitable for inclusion as an adjunct material.

The precise nature of these additional components, and levels of incorporation thereof, will depend on the physical form of the composition and the nature of the operation for which it is to be used.

a. Surfactants

The compositions of the present disclosure may comprise surfactant. Surfactant may be used in substitution or in addition to emulsifiers in the process of making the benefit agent delivery particles. Surfactants can aid in the emulsifying step. The population of delivery particle compositions may comprise one or more surfactants.

The compositions of the present disclosure may replace or reduce the amount of emulsifier used, or may include from about 0.1% to about 70%, or from about 2% to about 60%, or from about 5% to about 50%, by weight of the composition, of surfactant.

Surfactants may include anionic surfactant, nonionic surfactant, zwitterionic surfactant, cationic surfactant, amphoteric surfactant, or combinations thereof. The surfactants may comprise linear alkyl benzene sulfonate, alkyl ethoxylated sulfate, alkyl sulfate, nonionic surfactant such as ethoxylated alcohol, amine oxide, or mixtures thereof. The surfactants may be, at least in part, derived from natural sources, such as natural feedstock alcohols.

Suitable anionic surfactants may include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. The anionic surfactants may be linear, branched, or combinations thereof. Preferred surfactants include linear alkyl benzene sulfonate (LAS), alkyl ethoxylated sulfate (AES), alkyl sulfates (AS), or mixtures thereof. Other suitable anionic surfactants include branched modified alkyl benzene sulfonates (MLAS), methyl ester sulfonates (MES), sodium lauryl sulfate (SLS), sodium lauryl ether sulfate (SLES), and/or alkyl ethoxylated carboxylates (AEC). The anionic surfactants may be present in acid form, salt form, or mixtures thereof. The anionic surfactants may be neutralized, in part or in whole, for example, by an alkali metal (e.g., sodium) or an amine (e.g., monoethanolamine).

The surfactant system may include nonionic surfactant. Suitable nonionic surfactants include alkoxylated fatty alcohols, such as ethoxylated fatty alcohols. Other suitable nonionic surfactants include alkoxylated alkyl phenols, alkyl phenol condensates, mid-chain branched alcohols, mid-chain branched alkyl alkoxylates, alkylpolysaccharides (e.g., alkylpolyglycosides), polyhydroxy fatty acid amides, ether capped poly(oxyalkylated) alcohol surfactants, and mixtures thereof. The alkoxylate units may be ethyleneoxy units, propyleneoxy units, or mixtures thereof. The nonionic surfactants may be linear, branched (e.g., mid-chain branched), or a combination thereof. Specific nonionic surfactants may include alcohols having an average of from about 12 to about 16 carbons, and an average of from about 3 to about 9 ethoxy groups, such as C12-C14 EO7 nonionic surfactant.

Suitable zwitterionic surfactants may include any conventional zwitterionic surfactant, such as betaines, including alkyl dimethyl betaine and cocodimethyl amidopropyl betaine, $C_8$ to $C_{18}$ (for example from $C_{12}$ to $C_{18}$) amine oxides (e.g., $C_{12-14}$ dimethyl amine oxide), and/or sulfo and hydroxy betaines, such as N-alkyl-N,N-dimethylammino-1-propane sulfonate where the alkyl group can be $C_8$ to $C_{18}$, or from $C_{10}$ to $C_{14}$. The zwitterionic surfactant may include amine oxide.

Depending on the formulation and/or the intended end-use, the composition may be substantially free of certain surfactants. For example, intended end uses of the composition constituting the population of benefit agent particles such as a slurry for inclusion in liquid fabric enhancer, such as fabric softeners, in certain constructs may be substantially free of anionic surfactant, as such surfactants in certain formulations may negatively interact with cationic ingredients.

b. Deposition Aid

The compositions of the present disclosure may comprise a deposition aid. Deposition aids can facilitate deposition of benefit agent delivery particles, conditioning actives, perfumes, or combinations thereof, improving the performance benefits of the compositions and/or allowing for more efficient formulation of such benefit agents. The composition may comprise, by weight of the composition, from 0.0001% to 3%, preferably from 0.0005% to 2%, more preferably from 0.001% to 1%, or from about 0.01% to about 0.5%, or from about 0.05% to about 0.3%, of a deposition aid. The deposition aid may be a cationic or amphoteric polymer, preferably a cationic polymer.

Cationic polymers, in general, and their methods of manufacture are known in the literature. Suitable cationic polymers may include quaternary ammonium polymers known the "Polyquaternium" polymers, as designated by the International Nomenclature for Cosmetic Ingredients, such as Polyquaternium-6 (poly(diallyldimethylammonium chloride), Polyquaternium-7 (copolymer of acrylamide and diallyldimethylammonium chloride), Polyquaternium-10 (quaternized hydroxyethyl cellulose), Polyquaternium-22 (copolymer of acrylic acid and diallyldimethylammonium chloride), and the like.

The deposition aid may be selected from the group consisting of polyvinylformamide, partially hydroxylated polyvinylformamide, polyvinylamine, polyethylene imine, ethoxylated polyethylene imine, polyvinylalcohol, polyacrylates, and combinations thereof. The cationic polymer may comprise a cationic acrylate.

Deposition aids can be added concomitantly with particles (at the same time with, e.g., encapsulated benefit agents) or directly/independently in the fabric treatment composition. The weight-average molecular weight of the polymer may be from 500 to 5000000 or from 1000 to 2000000 or from 2500 to 1500000 Dalton, as determined by size exclusion chromatography relative to polyethylene oxide standards using Refractive Index (RI) detection. The weight-average molecular weight of the cationic polymer may be from 5000 to 37500 Dalton.

Process of Making Composition Combinations with Adjunct Materials

The present disclosure relates to processes for making any of the compositions described herein. The process of making a composition may comprise the step of combining a benefit agent delivery particle as described herein with an adjunct material.

The particles may be combined with such one or more adjunct materials such as adjuncts materials when the particles are in one or more forms, including an aqueous slurry form, neat particle form, agglomerates, cakes, dewatered solids, and/or spray dried particle form. The particles may be combined with adjunct materials by methods that include mixing and/or spraying.

The compositions of the present disclosure can be formulated into any suitable form and prepared by any process chosen by the formulator. The particles and adjunct materials may be combined in a batch process, in a circulation loop process, and/or by an in-line mixing process. Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders.

Test Methods

It is understood that the test methods that are disclosed in the Test Methods Section of the present application should be used to determine the respective values of the parameters of the subject matter described and claimed herein.

Extraction of Delivery Particles from Finished Products.

Except where otherwise specified herein, the preferred method to isolate delivery particles from finished products is based on the fact that the density of most such delivery particles is different from that of water. The finished product is mixed with water in order to dilute and/or release the delivery particles. The diluted product suspension is centrifuged to speed up the separation of the delivery particles. Such delivery particles tend to float or sink in the diluted solution/dispersion of the finished product. Using a pipette or spatula, the top and bottom layers of this suspension are removed and undergo further rounds of dilution and centrifugation to separate and enrich the delivery particles. The delivery particles are observed using an optical microscope equipped with crossed-polarized filters or differential interference contrast (DIC), at total magnifications of 100× and 400×. The microscopic observations provide an initial indication of the presence, size, quality and aggregation of the delivery particles.

For extraction of delivery particles from a liquid fabric enhancer finished product conduct the following procedure:
  a) Place three aliquots of approximately 20 ml of liquid fabric enhancer into three separate 50 ml centrifuge tubes and dilute each aliquot 1:1 with DI water (e.g. 20 ml fabric enhancer+20 ml DI water), mix each aliquot well and centrifuge each aliquot for 30 minutes at approximately 10000×g.
  b) After centrifuging per Step 1, discard the bottom water layer (around 10 ml) in each 50 ml centrifuge tube then add 10 ml of DI water to each 50 ml centrifuge tube.
  c) For each aliquot, repeat the process of centrifuging, removing the bottom water layer and then adding 10 ml of DI water to each 50 ml centrifuge tube two additional times.
  d) Remove the top layer with a spatula or a pipette, and
  e) Transfer this top layer into a 1.8 ml centrifuge tube and centrifuge for 5 minutes at approximately 20000×g.
  f) Remove the top layer with a spatula and transfer into a new 1.8 ml centrifuge tube and add DI water until the tube is completely filled, then centrifuge for 5 minutes at approximately 20000×g.
  g) Remove the bottom layer with a fine pipette and add DI water until tube is completely filled and centrifuge for 5 minutes at approximately 20000×g.
  h) Repeat step 7 for an additional 5 times (6 times in total).

If both a top layer and a bottom layer of enriched delivery particles appear in the above described step 1, then, immediately move to step 3 (i.e., omit step 2) and proceed steps with steps 4 through 8. Once those steps have been completed, also remove the bottom layer from the 50 ml centrifuge tube from step 1, using a spatula or/and a pipette. Transfer the bottom layer into a 1.8 ml centrifuge tube and centrifuge 5 min at approximately 20000×g. Remove the bottom layer in a new tube and add DI water until the tube is completely filled then centrifuge for 5 minutes approximately 20000×g. Remove the top layer (water) and add DI water again until the tube is full. Repeat this another 5 times (6 times in total). Recombine the delivery particle enriched and isolated top and bottom layers back together.

If the fabric enhancer has a white color or is difficult to distinguish the delivery particle enriched layers add 4 drops of dye (such as Liquitint Blue JH 5% premix from Milliken & Company, Spartanburg, South Carolina, USA) into the centrifuge tube of step 1 and proceed with the isolation as described.

For extraction of delivery particles from solid finished products that disperse readily in water, mix 1 L of DI water with 20 g of the finished product (e.g. detergent foams, films, gels and granules; or water-soluble polymers; soap flakes and soap bars; and other readily water-soluble matrices such as salts, sugars, clays, and starches). When extracting delivery particles from finished products which do not disperse readily in water, such as waxes, dryer sheets, dryer bars, and greasy materials, it may be necessary to add detergents, agitation, and/or gently heat the product and diluent in order to release the delivery particles from the matrix. The use of organic solvents or drying out of the delivery particles should be avoided during the extraction steps as these actions may damage the delivery particles during this phase.

For extraction of delivery particles from liquid finished products which are not fabric softeners or fabric enhancers (e.g., liquid laundry detergents, liquid dish washing detergents, liquid hand soaps, lotions, shampoos, conditioners, and hair dyes), mix 20 ml of finished product with 20 ml of DI water. If necessary, NaCl (e.g., 100-200 g NaCl) can be added to the diluted suspension in order to increase the density of the solution and facilitate the delivery particles floating to the top layer. If the product has a white color which makes it difficult to distinguish the layers of delivery particles formed during centrifugation, a water-soluble dye can be added to the diluent to provide visual contrast.

The water and product mixture is subjected to sequential rounds of centrifugation, involving removal of the top and bottom layers, re-suspension of those layers in new diluent, followed by further centrifugation, isolation and re-suspension. Each round of centrifugation occurs in tubes of 1.5 to 50 ml in volume, using centrifugal forces of up to 20,000×g, for periods of 5 to 30 minutes. At least six rounds of centrifugation are typically needed to extract and clean sufficient delivery particles for testing. For example, the initial round of centrifugation may be conducted in 50 ml tubes spun at 10,000×g for 30 mins, followed by five more rounds of centrifugation where the material from the top and bottom layers is resuspended separately in fresh diluent in 1.8 ml tubes and spun at 20,000×g for 5 mins per round.

If delivery particles are observed microscopically in both the top and bottom layers, then the delivery particles from these two layers are recombined after the final centrifugation step, to create a single sample containing all the delivery particles extracted from that product. The extracted delivery particles should be analyzed as soon as possible but may be stored as a suspension in DI water for up to 14 days before they are analyzed.

One skilled in the art will recognize that various other protocols may be constructed for the extraction and isolation of delivery particles from finished products and will recognize that such methods require validation via a comparison of the resulting measured values, as measured before and after the delivery particles' addition to and extraction from finished product.

Benefit Agent Leakage

The amount of benefit agent leakage from the delivery particles is determined according to the following method:
a.) Obtain two samples of the raw material slurry of delivery particles in such amounts so that 1 g of encapsulated perfume (e.g., 1 g perfume oil, not including the shell and/or partitioning modifier, if present) is present in each sample (or other amount as so indicated).
b.) Add one sample of the raw material slurry of delivery particles to a suitable amount of the product matrix (e.g., a liquid detergent product or an LFE product) in which the delivery particles will be employed to form 100 g total (e.g., 5 g slurry and 95 g product matrix) and label the mixture as Sample 1. Immediately use the second sample of raw material delivery particle slurry in Step d below, in its neat form without contacting product matrix, and label it as Sample 2.
c.) Age the delivery-particle-containing product matrix (Sample 1) for one week at 35° C. (or other time and/or temperature, as so indicated) in a sealed, glass jar.
d.) Using filtration, recover the delivery particles from both samples. The delivery particles in Sample 1 (in product matrix) are recovered after the aging step. The delivery particles in Sample 2 (neat raw material slurry) are recovered at the same time that the aging step began for sample 1.
e.) Treat the recovered delivery particles with a solvent to extract the benefit agent materials from the delivery particles.
f.) Analyze the solvent containing the extracted benefit agent from each sample, via chromatography. Integrate the resultant benefit agent peak areas under the curve and sum these areas to determine the total quantity of benefit agent extracted from each sample.
g.) Determine the percentage of benefit agent leakage by calculating the difference in the values obtained for the total quantity of benefit agent extracted from Sample 2 minus Sample 1, expressed as a percentage of the total quantity of benefit agent extracted from Sample 2, as represented in the equation below:

Percentage of Benefit Agent Leakage=(Sample 2−Sample 1/Sample 2)×100

Viscosity

Viscosity of liquid finished product is measured using an AR 550 rheometer/viscometer from TA instruments (New Castle, DE, USA), using parallel steel plates of 40 mm diameter and a gap size of 500 μm. The high shear viscosity at 20 $s^{-1}$ and low shear viscosity at 0.05 $s^{-1}$ is obtained from a logarithmic shear rate sweep from 0.1 $s^{-1}$ to 25 $s^{-1}$ in 3 minutes time at 21° C.

Perfume, Perfume Raw Materials (PRMs), and/or Partitioning Modifier

A. Identity and Total Quantity

To determine the identity and to quantify the total weight of perfume, perfume ingredients, or Perfume Raw Materials (PRMs), or partitioning modifier in the capsule slurry, and/or encapsulated within the delivery agent encapsulates, Gas Chromatography with Mass Spectroscopy/Flame Ionization Detector (GC-MS/FID) is employed. Suitable equipment includes: Agilent Technologies G1530A GC/FID; Hewlett Packer Mass Selective Device 5973; and 5%-Phenyl-methylpolysiloxane Column J&W DB-5 (30 m length×0.25 mm internal diameter×0.25 μm film thickness). Approximately 3 g of the finished product or suspension of delivery encapsulates, is weighed and the weight recorded, then the sample is diluted with 30 mL of DI water and filtered through a 5.0 μm pore size nitrocellulose filter membrane. Material captured on the filter is solubilized in 5 mL of ISTD solution (25.0 mg/L tetradecane in anhydrous alcohol) and heated at 60° C. for 30 minutes. The cooled solution is filtered through 0.45 μm pore size PTFE syringe filter and analyzed via GC-MS/FID. Three known perfume oils are used as comparison reference standards. Data Analysis involves summing the total area counts minus the ISTD area counts and calculating an average Response Factor (RF) for the 3 standard perfumes. Then the Response Factor and total area counts for the product encapsulated perfumes are used along with the weight of the sample, to determine the total weight percent for each PRM in the encapsulated perfume. PRMs are identified from the mass spectrometry peaks.

B. Amount of Non-Encapsulated Material

In order to determine the amount of non-encapsulated perfume and (optionally) partitioning modifier material in a composition such as a slurry, the following equipment can be used for this analysis, using the analysis procedure provided after the table.

| Gas chromatograph/MS | Agilent GC6890 equipped with Agilent 5973N mass spectrometer or equivalent, capillary column operation, quantitation based on extracted ion capability, autosampler |
|---|---|
| Column for GC-MS | 30 m × 0.25 mm nominal diameter, 0.25 μm film thickness, J&W 122-5532 DB-5, or equivalent. |

To prepare a perfume standard in ISS Hexane, weigh 0.050+/−0.005 g of the desired PMC perfume oil into a 50 mL volumetric flask (or other volumetric size recalculating g of perfume oil to add). Fill to line with ISS Hexane solution from above. The ISS Hexane is a 0.1 g of Tetradecane in 4 liters of hexane.

To prepare a 5% surfactant solution, weigh 50 g+/−1 g of the sodium dodecyl sulphate in a beaker and, using purified water, transfer quantitatively to a 1 liter volumetric flask, and ensure the surfactant is fully dissolved.

To prepare the sample of the PMC composition (e.g., a slurry), confirm the composition (e.g., a slurry) is well mixed; mix if necessary. Weigh 0.3+/−0.05 g of composition sample onto the bottom of a 10 mL vial. Avoid composition on the wall of the vial.

To operate the instrument, determine a target ion for quantification for each PRM (and optionally partitioning modifier) along with a minimum of one qualifier ion, preferably two. Calibration curves are generated from the Perfume standard for each PRM. Utilizing the sample weight and individual PRM weight %, the integration of the extracted ion (EIC) for each PRM and the amount are plotted or recorded.

The amount of free oil is determined from the response of each PRM versus the calibration curve and summed over all the different perfume materials and optionally the partitioning modifier.

C. Determination of Encapsulated Material

The determination of the encapsulated oil and optionally the partitioning modifier is done by the subtraction of the weight of free/non-encapsulated oil found in the composition from the amount by weight of total oil found in the composition (e.g. a slurry).

Analytical Determination of Wall Materials

This method determines the amount of wall material. First, the wall material of particles with size larger than 0.45 micrometer are isolated via dead-end filtration. Subsequent analysis by thermogravimetric analysis allows for elimination of inorganic material and other (organic) raw material slurry ingredients.

A. Sample Preparation

The procedure applies dead-end filtration to eliminate soluble fractions of the sample. Different solvents in succession are used to maximize the removal of interfering substances prior to TGA analysis.

The following materials and/or equipment are used:

Filtration Equipment
  Vacuum pump: Millipore Model WP6122050 or equivalent.
  Thick walled vacuum tubing to connect pump with filtration device.
  Filtrations flasks 500 or 1000 ml.
  Filtration cup: e.g. 250 ml Millipore Filtration funnel ("Milli Cup"), filtration material: 0.45 micrometer membrane, solvent resistant.
  Sealable Plastic container to contain the filtration device while weighing.
  Standard laboratory glassware (glass beakers 100-250 ml, measuring cylinders 50-250 ml).

Drying Equipment
  Vacuum oven and vacuum pump (settings 60-70 C/vacuum: 30-inch Mercury vacuum).
  Desiccator or constant humidity chamber (keeping residues under controlled environment during cooling.

Solvents
  All solvents: Analytical Grade minimum: 2-Propanol, Acetone, Chloroform The filtration procedure is as follows: To prepare the filtration device, record the weight of a pre-dried filtration device (e.g. Milli cup filter) down to 0.1-0.2 mg. Pre-drying involves the same drying steps as done for the filter after filtration is completed.

Filter the sample by weighing between 1 and 2 grams of Slurry Raw Material (note weight down to 0.1-0.2 mg) into a glass beaker (250 ml), or directly into the filtration device. Add 20 ml of deionized water and swirl to homogenize the sample. Add 80 ml of isopropyl alcohol and homogenize sample with solvent; use heating to flocculate the sample. Put the filtration device onto a filtration bottle, and start up filtration with vacuum. After filtration is complete, add 100 ml Chloroform. Continue filtration. Add 10-20 ml Acetone and filter through the membrane to remove traces of chloroform. Remove the filter from the filtration system and dry it in a vacuum oven. After cooling, weigh the filter and record the weight.

Calculate the percent residue (gravimetric residue) by dividing the weight difference of Filter+Residue and Filter weight only (=net weight of residue after filtration) by the Raw Material Slurry sample weight and multiply by 100 to obtain % units. Continue with the measurement of % Residue via TGA analysis.

Thermo Gravimetric Analysis (TGA) is performed with the following equipment and settings: TGA: TA instruments Discovery TGA; Pans: Sealed Aluminum; Purge: N2 at 50 ml/min; Procedure: Ramp 10° C./min to 500° C.; TGA is coupled to a Nicolet Nexus 470 FTIR spectrometer for evolved gas.

For TGA data analysis, the weight loss between 35° and 500° C. is due to decomposition of polymer wall material of the perfume micro capsules and still residual (burned) perfume compounds. For calculation of insoluble polymer fraction this weight loss is used. At 500° C. there is still a residue which is un-burned material and should be considered when calculating the insoluble polymer fraction.

Analytical Determination of the Core:Wall Ratio

When the amount of core and wall material inputs are not readily available, the core:wall ratio of the encapsulates may be determined analytically using the methods described herein.

More specifically, the methods above allow determination (in weight) the amounts of perfume, partitioning modifier, and wall materials in the perfume capsule composition (e.g., a slurry) and can be used to calculate the core:wall ratio. This is done by dividing the total amount (by weight) of perfume plus partitioning modifier found in the composition divided by the amount (by weight) of cross-linked wall material found in the composition Test Method for Determining log P The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Volume Weighted Particle Size and Size Distribution

The volume-weighted capsule size distribution is determined via single-particle optical sensing (SPOS), also called optical particle counting (OPC), using the AccuSizer 780 AD instrument and the accompanying software CW788 version 1.82 (Particle Sizing Systems, Santa Barbara, California, U.S.A.), or equivalent. The instrument is configured with the following conditions and selections: Flow Rate=1 ml/sec; Lower Size Threshold=0.50 µm; Sensor Model Number=Sensor Model Number=LE400-05 or equivalent; Autodilution=On; Collection time=60 sec; Number channels=512; Vessel fluid volume=50 ml; Max coincidence=9200. The measurement is initiated by putting the sensor into a cold state by flushing with water until background counts are less than 100. A sample of delivery capsules in suspension is introduced, and its density of capsules adjusted with DI water as necessary via autodilution to result in capsule counts of at least 9200 per ml. During a time period of 60 seconds the suspension is analyzed. The resulting volume-weighted PSD data are plotted and recorded, and the values of the desired volume-weighted particle size (e.g., the median/50th percentile, 5th percentile, and/or 90th percentile) are determined.

The broadness index can be calculated by determining the delivery particle size at which 90% of the cumulative particle volume is exceeded (90% size), the particle size at which 5% of the cumulative particle volume is exceeded (5% size), and the median volume-weighted particle size (50% size: 50% of the particle volume both above and below this size).

Broadness Index=((90% size)−(5% size))/50% size.

Alternatively, where indicated, Broadness Index (95% size) can be calculated on the basis of determining the particle size at which 95% of the cumulative particle volume is exceeded (95% size), the particle size at which 5% of the cumulative particle volume is exceeded (5% size), and the median volume-weighted particle size (50% size-50% of the particle volume both above and below this size). Broadness Index (5)=((95% size)−(5% size))/50% size.

Fracture Strength Test Method

To measure average Fracture Strength for the population, and/or and determine Delta Fracture Strength, three different measurements are made: i) the volume-weighted capsule size distribution; ii) the diameter of 10 individual capsules within each of 3 specified size ranges (and/or 30 individual capsules at the median volume-weighted particle size, if average Fracture Strength is to be determined), and; iii) the rupture-force of those same 30 individual capsules.

a.) The volume-weighted capsule size distribution is determined as described above. The resulting volume-weighted PSD data are plotted and recorded, and the values of the median, $5^{th}$ percentile, and $90^{th}$ percentile are determined.

b.) The diameter and the rupture-force value (also known as the bursting-force value) of individual capsules are measured via a custom computer-controlled micromanipulation instrument system which possesses lenses and cameras able to image the delivery capsules, and which possess a fine, flat-ended probe connected to a force-transducer (such as the Model 403A available from Aurora Scientific Inc, Canada) or equivalent, as described in: Zhang, Z. et al. (1999) "Mechanical strength of single microcapsules determined by a novel micromanipulation technique." *J. Microencapsulation*, vol 16, no. 1, pages 117-124, and in: Sun, G. and Zhang, Z. (2001) "Mechanical Properties of Melamine-Formaldehyde microcapsules." *J. Microencapsulation*, vol 18, no. 5, pages 593-602, and as available at the University of Birmingham, Edgbaston, Birmingham, UK.

c.) A drop of the delivery capsule suspension is placed onto a glass microscope slide, and dried under ambient conditions for several minutes to remove the water and achieve a sparse, single layer of solitary capsules on the dry slide. Adjust the concentration of capsules in the suspension as needed to achieve a suitable capsule density on the slide. More than one slide preparation may be needed.

d.) The slide is then placed on a sample-holding stage of the micromanipulation instrument. Thirty benefit delivery capsules on the slide(s) are selected for measurement, such that there are ten capsules selected within each of three pre-determined size bands. Each size band refers to the diameter of the capsules as derived from the Accusizer-generated volume-weighted PSD. The three size bands of capsules are: the Median/$50^{th}$ Percentile Diameter+/−2 µm; the $5^{th}$ Percentile Diameter+/−2 µm; and the $90^{th}$ Percentile Diameter+/−2 µm Capsules which appear deflated, leaking or damaged are excluded from the selection process and are not measured.

i. If enough capsules are not available at a particular size band+/−2 µm, then the size band may be increased to +/−5 µm.
   ii. If average Fracture Strength for the population is to be determined, then 30 (or more) capsules at the median/50th Percentile size band may be measured.

e.) For each of the 30 selected capsules, the diameter of the capsule is measured from the image on the micromanipulator and recorded. That same capsule is then compressed between two flat surfaces, namely the flat-ended force probe and the glass microscope slide, at a speed of 2 µm per second, until the capsule is ruptured. During the compression step, the probe force is continuously measured and recorded by the data acquisition system of the micromanipulation instrument.

f.) The cross-sectional area is calculated for each of the selected capsules, using the diameter measured and assuming a spherical capsule ($\pi r^2$, where r is the radius of the capsule before compression). The rupture force is determined for each selected capsule from the recorded force probe measurements, as demonstrated in Zhang, Z. et al. (1999) "Mechanical strength of single microcapsules determined by a novel micromanipulation technique." *J. Microencapsulation*, vol 16, no. 1, pages 117-124, and in: Sun, G. and Zhang, Z. (2001) "Mechanical Properties of Melamine-Formaldehyde microcapsules." *J. Microencapsulation*, vol 18, no. 5, pages 593-602.

g.) The Fracture Strength of each of the 30 capsules is calculated by dividing the rupture force (in Newtons) by the calculated cross-sectional area of the respective capsule.

h.) Average Fracture Strength for the population is determined by averaging the Fracture Strength values of at least 30 capsules at the Median/50th Percentile size band.

The Delta Fracture Strength is calculated as follows:

$$\text{Delta Fracture Strength (\%)} = \frac{FS@d_5 - FS@d_{90}}{FS@d_{50}} * 100$$

where FS at $d_i$ is the FS of the capsules at the percentile i of the volume-weighted size distribution.

EXAMPLES

The examples provided below are intended to be illustrative in nature and are not intended to be limiting.

Example 1. Exemplary Synthesis of Delivery Particles

Exemplary synthesis processes for different delivery particles are provided below. Details for the materials used are provided in Table 1.

A. Process Description for Preparing 18 or 36 Micron Capsules—98:2 Core to Wall Ratio "(C:W)" and 40% IPM with CN975.

To a 1 L capacity water jacketed stainless steel reactor, 143.12 grams of perfume oil and 137.45 grams of isopropyl myristate were added and allowed to mix with the aid of a high shear mixer fitted with a mill blade, under a nitrogen environment. The solution was heated to 35° C. before introducing 0.33 grams of Vazo67 (initiator) and the total mixture was subsequently heated to 70° C. and was maintained at that temperature for 45 minutes before cooling the system down to 50° C. As soon as the temperature was reached, a solution, prepared separately, containing 63.05 grams of perfume oil, 0.075 grams of CD9055, 0.075 grams of TBAEMA, and 6.23 grams of CN975 was introduced into the reactor and the total mixture was allowed to mix for 10 min while at 50° C. The water phase, consisting of 107 grams of emulsifier (5% solution of PVOH 540), 340.03 grams of RO water, 0.22 grams of V-501, and 0.21 grams of NaOH (21% solution) was then added to the reactor, after stopping agitation. Milling ensued after the addition of the water phase until the particle size was reached. The emulsion was then heated first to 75° C. and maintained at that temperature for 240 minutes and then heated to 95° C. for 360 min before cooling it down to 25° C. At that point, the slurry was evacuated from the reactor into a container to add the rheology modifier (Xanthan gum 1.59 grams) and preservative (Acticide BWS-10; 0.61 grams). The rheology modifier was allowed to mix in for 30 min. The preservative was added last and allowed to mix for 5-10 min. The finished slurry was then characterized and tested as deemed fit.

Core:Wall Weight Ratio—Sample Calculation

The core:wall weight ratio is determined by dividing the weight of the total core material inputs (e.g., perfume oil and partitioning modifier) by the weight of the total wall material inputs (e.g., wall monomers and initiators). Alternatively, the relative percentage of core material in the particle population can be determined by dividing the weight of the total core material inputs by the sum of the total weight of the core material inputs plus the total weight of the wall material inputs and multiplying by 100; the remaining percentage (100-% core) is the relative percentage of the wall material—these numbers may then be expressed as a ratio. Similarly, the relative percentage of wall material in the particle population can be determined by dividing the total weight of the wall material inputs by the sum of the weights of the total core material inputs and the total wall material inputs and multiplying by 100.

A sample calculation for the "98:2" capsules formed by the example of this section is provided below, where the core comprises the perfume oil and a partitioning modifier (isopropyl myristate), and the wall comprises the wall monomers (CN975, CD9055, and TBAEMA) and the initiators (Vazo67 and V-501).

$$\% \text{ core} = \frac{(\text{perfume oil} + \text{partitioning modifier})}{(\text{perfume oil} + \text{partitioning modifier} + \text{wall monomers} + \text{initiators})} \times 100$$

$$\% \text{ core} = \frac{(143.12 \text{ g} + 63.05 \text{ g} + 137.45 \text{ g})}{(143.12 \text{ g} + 63.05 \text{ g} + 137.45 \text{ g} + 6.23 \text{ g} + 0.07 \text{ g} + 0.075 \text{ g} + 0.33 \text{ g} + 0.22 \text{ g})} \times 100$$

$$343.62$$

Delivery particle examples 1 and 3, as described below in Example 2, Table 2, are synthesized in substantial accordance with this process.

B. Process Description for Preparing 18 or 36 Micron Capsules—98:2 (C:W) and 40% IPM with SR295, EB140, EB895, TMPTA, SR444, or SR368

The process is the same as described in A, except CN975 was replaced with each of the indicated monomers. The weight demand in grams for the monomer was held constant.

Delivery particle examples 4-10, 12, 14, 16, 18, and 20, as described below in Example 2, Table 2, are synthesized in substantial accordance with this process.

C. Process Description for Preparing 36 Micron Capsules—98:2 (C:W) and 0% IPM with CN975, SR295, EB140, EB895, TMPTA, SR444, or SR368

The process is the same as described in A or B, except no IPM was used. For each of these examples, the demand for IPM was replaced with perfume oil regardless of which monomer was used.

Delivery particle examples 2, 11, 13, 15, 17, 19, and 21 as described below in Example 2, Table 2, are synthesized in substantial accordance with this process.

D. Process Description for Preparing 18 or 36 Micron Capsules—98:2 (C:W) and 40% IPM with SR295, EB140, EB895, TMPTA, SR444, SR368, and CN975 and No Minor Wall Monomers.

The same as A, except the 0.08 grams of CD9055 and 0.08 grams of TBAEMA were removed and the qty called for substituted with CN975 or other monomer, as indicated.

Delivery particle examples 25 and 26, as described below in Example 2, Table 2, are synthesized in substantial accordance with this process.

E. Process Description for Preparing 18 or 36 Micron Capsules—90:10 (C:W) and 40% IPM with CN975

The same as A, except CD9055 and 0.08 TBAEMA were removed and substituted with CN975, as indicated.

Delivery particle examples 22, 23, and 24, as described below in Example 2, Table 2, are synthesized in substantial accordance with this process.

TABLE 1

| Name | Company/City | Chemical Description |
| --- | --- | --- |
| CN975 | Sartomer Company, Exton, PA | hexafunctional urethane acrylate ester |
| EB140 | Allnex USA, Inc., Alpharetta, GA | ditrimethylolpropane tetraacrylate |
| SR295 | Sartomer Company, Exton, PA | pentaerythritol tetraacrylate |
| SR444 | Sartomer Company, Exton, PA | pentaerythritol triacrylate |
| TMPTA-1 | Allnex USA, Inc., Alpharetta, GA | trimethylolpropane triacrylate |
| SR368 | Sartomer Company, Exton, PA | tris (2-hydroxyethyl) isocyanurate triacrylate with aliphatic urethane acrylate |
| EB895 | Allnex USA, Inc., Alpharetta, GA | dipentaerythritol penta/hexa acrylate |
| Vazo 67 (initiator) | Chemours Company, Wilmington, DE | 2,2'-azobis (2-methylbutyronitrile) |
| TBAEMA | NovaSol North America Inc., Stoney Creek, ON, Canada | 2-(tert-butylamino) ethyl methacrylate |
| CD9055 | Sartomer Company, Exton, PA | acid acrylate |
| V-501 (initiator) | Sigma-Aldrich Corp. St. Louis, MO | 4,4'-azobis(4-cyanovaleric acid) |

Example 2. Properties of Various Delivery Particles

Various properties for delivery particles synthesized according to the processes described in Example 1 are provided below in Table 2. The value of "free oil" is given as a percentage (wt %) of the perfume oil that remains unencapsulated after formation of the capsules; lower free oil values indicate that the encapsulation process was more efficient (e.g., relatively greater amounts of perfume oil is encapsulated). Leakage is determined in a heavy-duty liquid (HDL) detergent product after one week of storage at 35° C.; the leakage values in Table 2 are provided in (%) and are determined by headspace analysis above neat product.

TABLE 2

| Delivery Particle Ex. # | Wt. Ratio (core to wall polymer) | Wall monomer | Functionality | % IPM | Particle Size (in microns +/−3 μm) | Broadness index | % Free oil | 1 wk leakage in HDL % |
|---|---|---|---|---|---|---|---|---|
| 1 | 98/2 | CN975 | 6 | 40 | 36.07 | 1.15 | 0.53 | 25.16 |
| 2 | 98/2 | CN975 | 6 | 0 | 34.78 | 1.15 | 22.31 | 100.00 |
| 3 | 98/2 | CN975 | 6 | 40 | 18.96 | 1.31 | 1.20 | 47.65 |
| 4 | 98/2 | EB140 | 4 | 40 | 35.21 | 1.23 | 1.95 | 80.76 |
| 5 | 98/2 | SR295 | 4 | 40 | 35.64 | 1.23 | 1.52 | 72.81 |
| 6 | 98/2 | SR444 | 3 | 40 | 36.07 | 1.10 | 9.83 | 100.00 |
| 7 | 98/2 | TMPTA-1 | 3 | 40 | 34.78 | 1.23 | 10.44 | 100.00 |
| 8 | 98/2 | SR368 | 3 | 40 | 36.07 | 1.14 | 8.05 | 100.00 |
| 9 | 98/2 | EB895 | 5/6 | 40 | 33.95 | 1.17 | 0.78 | 63.39 |
| 10 | 98/2 | SR368 | 3 | 40 | 19.66 | 1.29 | 5.22 | 100.00 |
| 11 | 98/2 | SR368 | 3 | 0 | 33.95 | 1.20 | 14.56 | 100.00 |
| 12 | 98/2 | EB895 | 5/6 | 40 | 17.63 | 1.30 | 2.06 | 82.64 |
| 13 | 98/2 | EB895 | 5/6 | 0 | 36.07 | 1.12 | 15.97 | 100.00 |
| 14 | 98/2 | EB140 | 4 | 40 | 17.63 | 1.20 | 11.02 | 100.00 |
| 15 | 98/2 | EB140 | 4 | 0 | 34.36 | 1.15 | 27.08 | 100.00 |
| 16 | 98/2 | SR444 | 3 | 40 | 18.50 | 1.30 | 3.31 | 92.34 |
| 17 | 98/2 | SR444 | 3 | 0 | 34.78 | 1.09 | 16.80 | 100.00 |
| 18 | 98/2 | TMPTA-1 | 3 | 40 | 19.42 | 1.21 | 10.63 | 100.00 |
| 19 | 98/2 | TMPTA-1 | 3 | 0 | 34.78 | 1.04 | 23.48 | 100.00 |
| 20 | 98/2 | SR295 | 4 | 40 | 18.73 | 1.34 | 1.64 | 80.50 |
| 21 | 98/2 | SR295 | 4 | 0 | 35.64 | 1.17 | 17.87 | 100.00 |
| 22 | 90/10 | CN975 | 6 | 40 | 19.66 | 1.32 | 0.13 | 13.70 |
| 23 | 90/10 | CN975 | 6 | 40 | 36.07 | 1.24 | 0.10 | 9.48 |
| 24 | 90/10 | CN975 | 6 | 0 | 36.96 | 1.25 | 0.83 | 100.00 |
| 25 | 98/2 | CN975 | 6 | 40 | 36.07 | 1.18 | 0.14 | 17.06 |
| 26 | 98/2 | SR295 | 4 | 40 | 36.96 | 1.17 | 0.21 | 46.14 |

In addition to the data presented in Table 2, results are presented graphically in FIGS. 1-4.

FIG. 1 is a graph depicting percent free oil of slurries prepared according to the invention, prepared at 18 and 36 micron diameter, and compared to 36 micron microcapsules in the absence of isopropyl myristate using (meth)acrylate monomers of various functionality as indicated.

Figure 2:
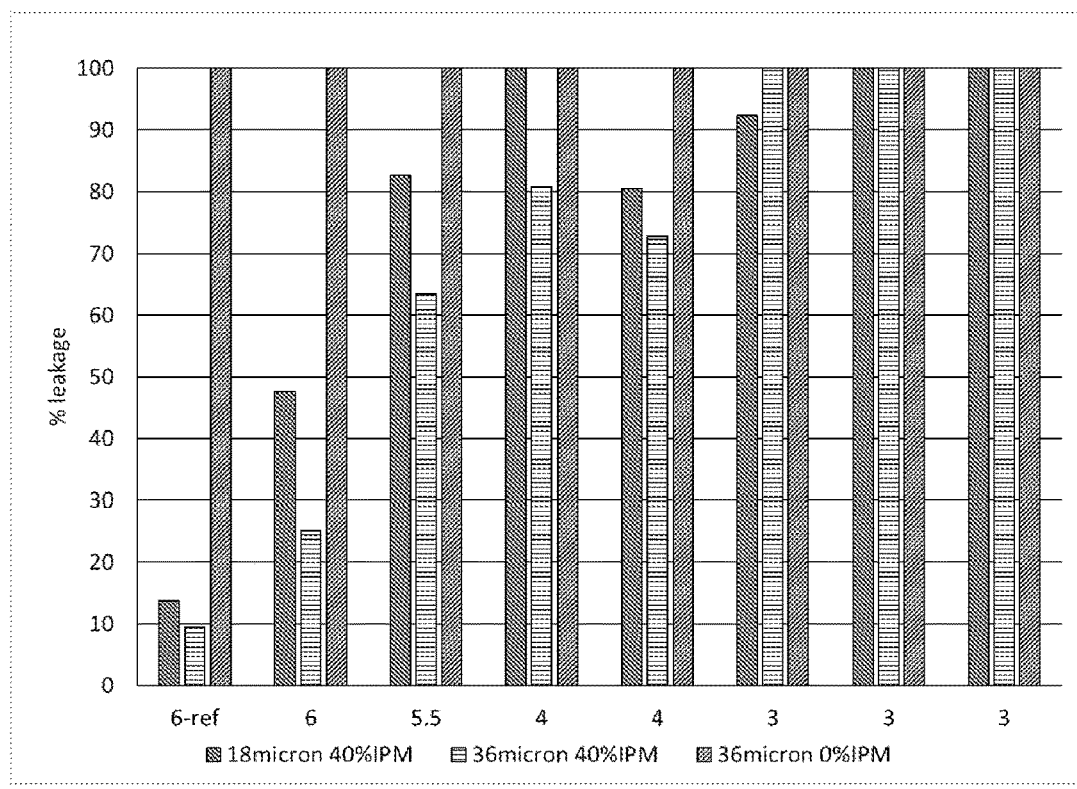
FIG. 2 is a graph depicting 1 week percent leakage of 18 and 36 micron diameter capsules with (meth)acrylate monomers of various functionality. Measurement is at 1 week with capsules dispersed in liquid laundry detergent measured at 35° C. The control is the same capsule at 36 microns without any isopropyl myristate.

FIG. 2 is a graph depicting 1 week percent leakage of 18 and 36 micron diameter capsules with (meth)acrylate monomers of various functionality. Measurement is at 1 week with capsules dispersed in liquid laundry detergent measured at 35° C. The control is the same capsule at 36 microns without any isopropyl myristate.

Figure 3:
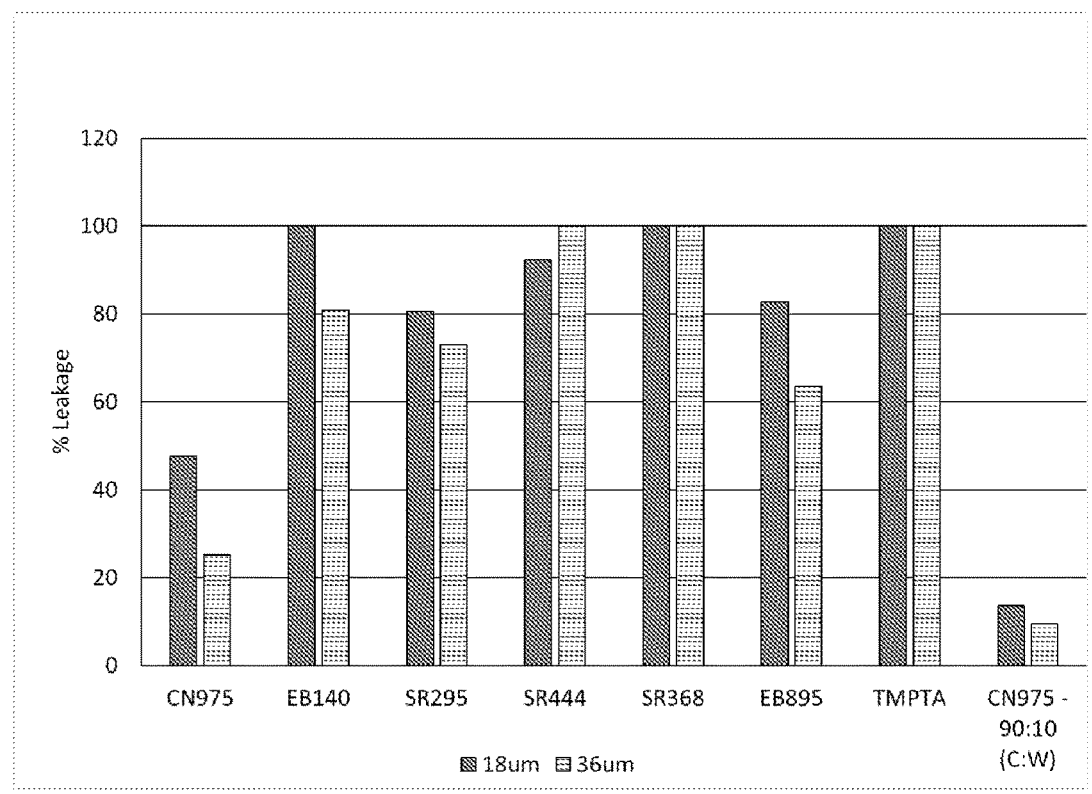
FIG. 3 is a graph depicting the percent leakage obtained from the slurries prepared at 18 micron versus 36 micron diameter using the wall material indicated.

FIG. 3 is a graph depicting the percent leakage obtained from the slurries prepared at 18 micron versus 36 micron diameter using the wall material indicated.

Figure 4:
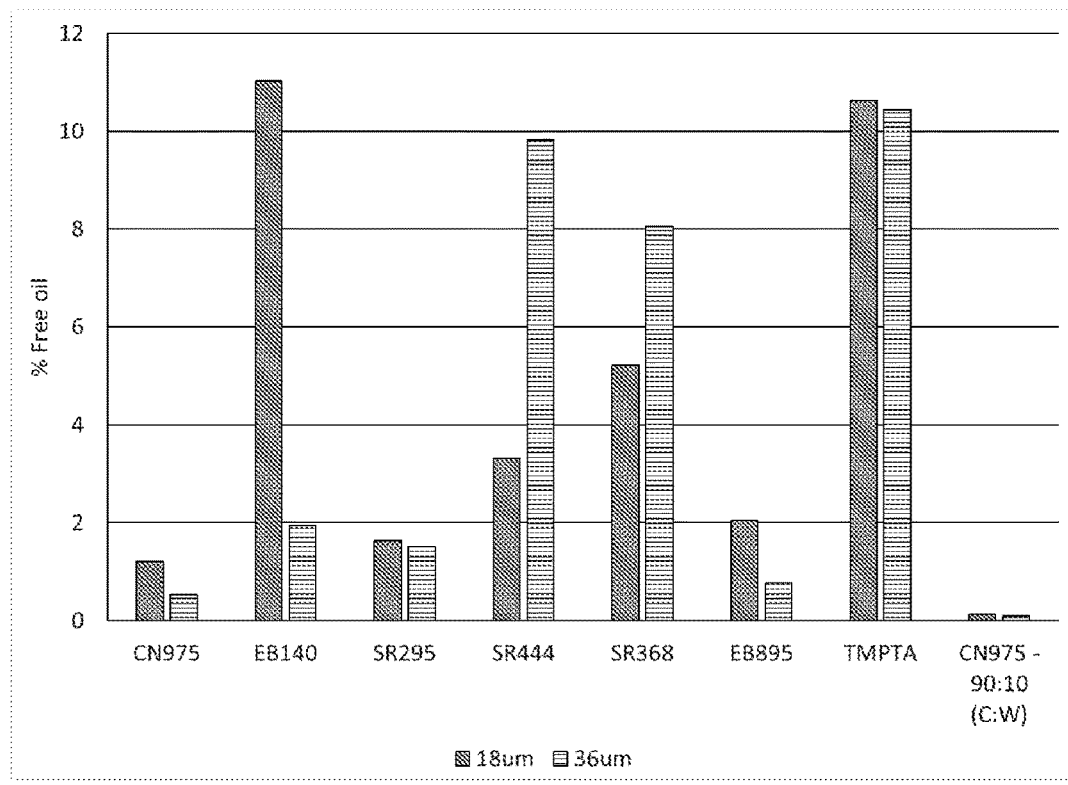
FIG. 4 is a graph depicting the % free oil of the slurries prepared at 18 and 36 micron diameter using various walls at 40% isopropyl myristate.

FIG. 4 is a graph depicting the % free oil of the slurries prepared at 18 and 36 micron diameter using various walls at 40% isopropyl myristate.

As shown in Table 2 and the figures, delivery particles having the preferred combination of monomer selection, core:polymer wall weight ratio, particle size, and partitioning modifier in accordance with the present disclosure tend to manifest relatively low levels of leakage.

Example 3. Performance Data

To compare delivery particles of different core:wall polymer ratios and of different sizes, samples of liquid fabric enhancers (7% ester quat as softening active) are prepared with the different particles. Each type of particle includes the same materials for their respective wall polymers, primarily CN975 monomer.

The same perfume is used in each particle type, and each core also include approximately 40 wt % of partitioning modifier (i.e., isopropyl myristate). The particles are added in respective amounts to provide 0.158 wt % of perfume, by weight of the fabric enhancer product composition.

Cotton terry tracers are treated (in combination with a mixed fabric load) with the fabric enhancers in a short cotton cycle in an automatic washing machine (1200 rpm), with the fabric enhancer being added during the last rinse cycle After the fabrics have been treated, expert perfumers perform an olfactive assessment for perfume intensity at the DRY and RUB touchpoints, and the scores at each touchpoint are averaged to give a score for that touchpoint. Scores are based on a perfume odor intensity scale from 0 to 100, where 0=no perfume odor, 25=slight perfume odor, 50=moderate perfume odor, 75=strong perfume odor, and 100=extremely strong perfume odor. To note, internal testing indicates that the advantages are not as evident at the wet touchpoint, nor on all fabrics. Additionally, headspace data is collected above the treated fabric using a solid phase microextraction (SPME) headspace approach with gas chromatography mass spectrometry (GCMS).

Descriptions of the delivery particles and the data results are provided below in Table 3. Leg Z includes delivery particles according to the present disclosure, whereas Legs W, X, and Y include comparative particles.

TABLE 3

| Delivery Particle | Approx. volume-weighted particle size | Core:wall polymer weight | Olfactive Assessment | | Headspace Analysis (nMol/L) | |
|---|---|---|---|---|---|---|
| Leg # | (microns) | ratio | DRY | RUB | DRY | RUB |
| W (comp.) | 18 | 90:10 | 52.5 | 58.8 | 59 | 115 |
| X (comp.) | 18 | 98:2 | 55 | 61.3 | 67.9 | 102 |
| Y (comp.) | 36 | 90:10 | 50 | 56.3 | 49.2 | 68.8 |
| Z | 36 | 98:2 | 62.5 | 70 | 116 | 138 |

As indicated in Table 3, delivery particles having a relatively high core wall polymer ratio (e.g., Legs 2 and 4, with 98:2 C:W ratio) generally outperform particles having a relatively lower ratio at one or both of the tested touchpoints.

Furthermore, by comparing the results of Leg 4 to the results of Leg 2, it is shown that delivery particles having a relatively larger particle size (e.g., 36 microns vs. 18 microns) perform relatively better at the indicated touchpoints.

Example 4. Exemplary Formulations—Liquid Fabric Enhancers

Table 4 shows exemplary formulations of compositions according to the present disclosure. Specifically, the following compositions are liquid fabric enhancer products.

TABLE 4

| | % Active (w/w) | | |
|---|---|---|---|
| Ingredient | Composition 1 | Composition 2 | Composition 3 |
| Quaternary ammonium ester material | 5% (Ester Quat 1)[1] | 7% (Ester Quat 2)[2] | 8% (Ester Quat 3)[3] |
| Delivery Particles* (w/ encapsulated fragrance) | 0.25% | 0.25% | 0.25% |
| Formic Acid | 0.045% | 0.045% | 0% |
| Hydrochloric acid | 0.01% | 0% | 0% |
| Preservative | 0.0045% | 0% | 0% |
| Chelant | 0.0071% | 0.0071% | 0% |
| Structurant | 0.10% | 0.30% | 0.1% |
| Antifoam | 0.008% | 0.00% | 0% |

[1]Ester Quat 1: Mixture of bis-(2-hydroxypropyl)-dimethylammonium methylsulfate fatty acid ester, (2-hydroxypropyl)-(1-methyl-2-hydroxyethyl)-dimethylammonium methylsulfate fatty acid ester, and bis-(1-methyl-2-hydroxyethyl)-dimethylammonium methylsulfate fatty acid ester, where the fatty acid esters are produced from a C12-C18 fatty acid mixture (REWOQUAT DIP V 20 M Conc, ex Evonik)
[2]Ester Quat 2: N,N-bis(hydroxyethyl)-N,N-dimethyl ammonium chloride fatty acid ester, produced from C12-C18 fatty acid mixture (REWOQUAT CI-DEEDMAC, ex Evonik)
[3]Ester Quat 3: Esterification product of fatty acids (C16-18 and C18 unsaturated) with triethanolamine, quaternized with dimethyl sulphate (REWOQUAT WE 18, ex Evonik)
*Delivery particles according to the present disclosure, e.g., Delivery Particle Ex. #1, Table 2, Example 2 above. The "% Active" provided is the amount of fragrance delivered to the composition.

Example 5. Exemplary Formulations—Laundry Additive Particles

Table 5 shows exemplary formulations of compositions according to the present disclosure. Specifically, the following compositions are laundry additive particles in the form of a pastille or "bead."

TABLE 5

| Ingredient | Ex. 1 | Ex. 2 | Ex. 3 | Ex. 4 | Ex. 5 | Ex. 6 |
|---|---|---|---|---|---|---|
| Polyethylene Glycol MW 8000[1] | 64% | 65% | 63% | 83.5% | 81.5% | 61% |
| Ester Quat[2] | 25% | 27% | 25% | — | — | 24% |
| CatHEC[3] | 3% | 3% | — | — | — | — |
| Perfume | — | — | — | 10.3% | 13.3% | 5% |
| Delivery Particles Slurry[4] | 8% | 4% | 12% | 5% | 5.2% | 10% |

[1]PLURIOL E8000 (ex BASF)
[2]Esterification product of fatty acids (C16-18 and C18 unsaturated) with triethanolamine, quaternized with dimethyl sulphate (REWOQUAT WE 18, ex Evonik)
[3]Cationically-modified hydroxyethylcellulose
[4]Fragrance delivery particles according to the present disclosure, e.g., the population formed in Example 1 above.
The % provided is the amount of aqueous slurry provided to the composition, where the slurry comprises about 45 wt % of delivery particles (core + shell).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A population of delivery particles, the delivery particles comprising a core and a polymer wall encapsulating said core, wherein:
   the core comprises an oily medium comprising a benefit agent and a partitioning modifier wherein the partitioning modifier comprises from 5% to 55% by weight of the core,
   the polymer wall comprises a (meth)acrylate polymer derived, at least in part, from
      (a) one or more oil-soluble or dispersible multifunctional (meth)acrylate monomers or oligomers and optionally at least one initiator,
   the one or more oil-soluble or dispersible multifunctional (meth)acrylate monomers or oligomers having at least six radical polymerizable functional groups, with the proviso that at least one of the radical polymerizable groups is acrylate or methacrylate;
      (b) a second monomer comprising a basic (meth)acrylate monomer,
   wherein the basic (meth)acrylate monomer selected from the group consisting of ethylaminoethyl acrylate, ethylaminoethyl methacrylate, aminoethyl acrylate, aminoethyl methacrylate, tertiarybutyl ethylamino acrylate, tertiarybutyl ethylamino methacrylate, tertiarybutyl aminoethyl acrylate, tertiarybutyl aminoethyl methacrylate, diethylamino acrylate, diethylamino methacrylate, diethylaminoethyl acrylate diethylaminoethyl methacrylate, dimethylaminoethyl acrylate and dimethylaminoethyl methacrylate;
   wherein the basic (meth)acrylate monomer comprises less than 2%, and more than 0%, by weight of the polymer wall; and,
      (c) a third monomer comprising an acidic (meth)acrylate monomer,
   wherein the acidic (meth)acrylate monomer selected from the group consisting of 2-carboxyethyl acrylate, 2-carboxyethyl methacrylate, 2-carboxypropyl acrylate, 2-carboxypropyl methacrylate, carboxyoctyl acrylate, carboxyoctyl methacrylate, Carboxy substituted aryl acrylates, 2-acryloyloxybenzoic acid, 3-acryloyloxybenzoic acid, 4-acryloyloxybenzoic acid, 2-methacryloyloxybenzoic acid, 3-methacryloyloxybenzoic acid, 4-methacryloyloxybenzoic acid, 4-acryloyloxyphenylacetic acid and 4-methacryloyloxyphenylacetic acid, wherein the acidic (meth)acrylate monomer comprises less than 2%, and more than 0%, by weight of the polymer wall;

said delivery particles having a core to polymer wall ratio by weight from about 96:4 to about 99.5:0.5; and, said delivery particles having a volume-weighted particle size from about 30 to about 50 microns.

2. The population of delivery particle according to claim 1, wherein the delivery particles comprise the core and polymer wall present in a weight ratio of from about 97:3 to about 99:1.

3. The population of delivery particles according to claim 1, wherein the radical polymerizable functional groups are each independently selected from the group consisting of acrylate and methacrylate.

4. The population of delivery particles according to claim 1, wherein the oil soluble or dispersible multifunctional (meth)acrylate monomer or oligomer comprises a hexafunctional aromatic urethane acrylate.

5. The population of delivery particles according to claim 1 wherein the polymer wall of the delivery particles further comprises a polymeric emulsifier entrapped in the polymer wall.

6. The population of delivery particles according to claim 1 wherein the (meth)acrylate polymer of the polymer wall is further derived, at least in part, from at least one free radical initiator, wherein the at least one free radical initiator comprises i) a water-soluble or water-dispersible free radical initiator, or, ii) a water-soluble or water-dispersible free radical initiator and an oil-soluble or oil-dispersible free radical initiator.

7. The population of delivery particles according to claim 6, wherein the free radical initiator is present in amount of from about 2% to about 50% by weight of the polymer wall.

8. The population of delivery particles according to claim 1 wherein the benefit per fragrance.

9. The population of delivery particles according to claim 1 wherein the partitioning modifier is selected from the group consisting of isopropyl myristate, vegetable oil, modified vegetable oil, mono-, di-, and tri-esters of C4-C24 fatty acids, dodecanophenone, lauryl laurate, methyl behenate, methyl laurate, methyl palmitate, methyl stearate, and mixtures thereof.

10. The population of delivery particles according to claim 1 wherein the population is characterized by an average volume weighted median fracture strength of from 0.2 to about 10 MPa.

11. The population of benefit agent delivery particles according to claim 1 wherein the polymer wall of the delivery particles further comprises a coating material, wherein the coating material is selected from the group consisting of poly(meth)acrylate, poly(ethylene-maleic anhydride), polyamine, wax, polyvinylpyrrolidone, polyvinylpyrrolidone co-polymers, polyvinylpyrrolidone-ethyl acrylate, polyvinylpyrrolidone-vinyl acrylate, polyvinylpyrrolidone methacrylate, polyvinylpyrrolidone/vinyl acetate, polyvinyl acetal, polyvinyl butyral, polysiloxane, poly(propylene maleic anhydride), maleic anhydride derivatives, co-polymers of maleic anhydride derivatives, polyvinyl alcohol, styrene-butadiene latex, gelatin, gum Arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, poly(vinyl pyrrolidone/methacrylamidopropyl trimethyl ammonium chloride), polyvinylpyrrolidone/vinyl acetate, polyvinyl pyrrolidone/dimethylaminoethyl methacrylate, polyvinyl amines, polyvinyl formamides, polyallyl amines, copolymers of polyvinyl amines, and mixtures thereof.

* * * * *